(12) United States Patent
Prendergast

(10) Patent No.: US 7,585,508 B1
(45) Date of Patent: Sep. 8, 2009

(54) FUSION PROTEINS COMPRISING CD4 AND THE MALARIA PARASITE MEROZOITE GLYCOPHORIN BINDING PROTEIN 130 (GBP-130)

(76) Inventor: Kenneth F. Prendergast, 56 Canning Road, Highbury, London N5 2JS (GB)

( * ) Notice: Subject to any disclaimer, the term of this patent is extended or adjusted under 35 U.S.C. 154(b) by 0 days.

(21) Appl. No.: 08/307,742

(22) PCT Filed: Mar. 10, 1993

(86) PCT No.: PCT/GB93/00505

§ 371 (c)(1),
(2), (4) Date: Sep. 8, 1994

(87) PCT Pub. No.: WO93/18160

PCT Pub. Date: Sep. 16, 1993

(30) Foreign Application Priority Data

| Mar. 11, 1992 | (GB) | ................................. | 9205276.0 |
| Jul. 8, 1992 | (GB) | ................................. | 9214481.5 |
| Jul. 24, 1992 | (GB) | ................................. | 9215829.4 |
| Sep. 16, 1992 | (GB) | ................................. | 9219562.7 |
| Mar. 3, 1993 | (GB) | ................................. | 9304311.5 |

(51) Int. Cl.
*A61K 39/00* (2006.01)
(52) U.S. Cl. ................................................. 424/192.1
(58) Field of Classification Search ................ 530/350; 435/172.3, 69.7; 536/23.4; 424/192.1, 272.1
See application file for complete search history.

(56) References Cited

U.S. PATENT DOCUMENTS

| 4,675,382 A | 6/1987 | Murphy ....................... 530/350 |
| 4,915,683 A | 4/1990 | Sieber ............................ 604/4 |
| 4,980,462 A | 12/1990 | Karlsson et al. ................ 536/53 |

FOREIGN PATENT DOCUMENTS

| EP | 073657 A1 | 3/1983 |
| EP | 298280 A2 | 1/1989 |
| WO | 8802030 | 3/1988 |
| WO | 8901940 | 3/1989 |
| WO | 8902922 | 4/1989 |
| WO | 8907652 | 8/1989 |
| WO | 8911860 | 12/1989 |

OTHER PUBLICATIONS

Tindall and Cooper, 1991, AIDS 5:1-14.*
Pantaleo et al., 1993, NEJM 328:327-335.*
Wei et al., 1995, Nature 373:117-122.*
Ho et al., 1995, Nature 373:123-126.*
Gomatos et al., 1990, J. Immunol. 144:4183-4188.*
Daar et al., 1990, Proc. Natl. Acad. Sci. USA 87:6574-6578.*
Husson et al., 1992, J. Pediatr. 121:627-633.*
Levy, J., 1993, Microbiol. Rev. 57:196,200,201.*

McKeating, J., et al. 1991. Recombinant CD4-selected human immunodeficiency virus type 1 variants with reduced gp120 affinity for CD4 and increased cell fusion capacity. J. Virol. 65(9):4777-4785.*
Willey, R. L., and M. A. Martin. 1993. Association of human immunodeficiency virus type 1 envelope glycoprotein with particles depends on interactions between the third variable and conserved regions of gp120. J. Virol. 67(6):3639-3643.*
McKeating, J. A., et al. 1993. Resistance of a human serum-selected human immunodeficiency virus type 1 escape mutant to neutralization by CD4 binding site monoclonal antibodies is conferred by a single amino acid change in gp120. J. Virol. 67(9):5216-5225.*
Moir, S., et al. 1997. CD4 deletion mutants evaluated for human immunodeficiency virus type 1 infectivity in a highly efficient system of expression and detection based on LTR-dependent reporter gene activation. J. Virol. Meth. 65:209-217.*
Strongin, W. 1992. Sensitivity, specificity, and predictive value of diagnostic tests: definitions and clinical applications. Laboratory Diagnosis of Viral Infections, Lennette, E. H., ed., Marcel Dekker, Inc. New York, New York, pp. 211-219.*
Wei, X., et al. 1995. Viral dynamics in human immunodeficiency virus type 1 infection. Nature 373:117-122.*
Ho, D. D., et al. 1995. Rapid turnover of plasma virions and CD4 lymphocytes in HIV-1 infection. Nature 373:123-126.*
Calvo, M., et al. 1991. Specific interactions of synthetic peptides derived from *P falciparum* merozoite proteins with human red blood cells. Pep. Res. 4(6):324-333.*
Suarez, J. E., et al. 2000. A GBP 130 derived peptide from *Plasmodium falciparum* binds to human erythrocytes and inhibits merozoite invasion in vitro. Mem. Inst. Oswaldo Cruz 95(4):495-501.*

(Continued)

*Primary Examiner*—J. S. Parkin

(57) ABSTRACT

Novel hybrid fusion peptides are disclosed. The novel peptides are formed by the fusion of two or more components. One component is a peptide sequence or variant of a peptide sequence derived from a malaria parasite merozoite peptide which has affinity for and binding capability to red blood cells.

In particular segments of the glycophorin binding peptide 130 (GBP130), are preferred for the first component. Also disclosed are alternative first components, the glycophorin binding peptide homologues (GBPH), or the erythrocyte binding antigen 175 (EBA175), or the *plasmodium vivax* Duffy receptor or the pre major merozoite surface antigen PMMSA or the (P200) peptide.

The first component peptide is fused to all or part of a peptide segment derived from the CD4 molecule or part thereof or variant thereof which shows binding affinity for the HIV virus.

The resulting fusion peptide being exemplified as
NH2-CD4-GBP130-COOH
1-371 201-774

Also disclosed are the methods of manufacture and means to use the novel hybrid peptides as clinical agents to treat, prevent or test for HIV infection.

9 Claims, 1 Drawing Sheet

OTHER PUBLICATIONS

Mizukami, T., et al. Binding region for human immunodeficiency virus (HIV) and epitopes for HIV-blocking monoclonal antibodies of the CD4 molecule defined by site-directed mutagenesis. Proc. Natl. Acad. Sci. USA 85:9273-9277.*

Brodsky, M. H., et al. 1990. Analysis of the site in CD4 that binds to the HIV envelope glycoprotein. J. Immunol. 144:3078-3086.*

Mizukami, T., et al. 1988, Binding region for human immunodeficiency virus (HIV) and epitopes for HIV-blocking monoclonal antibodies of the CD4 molecule defined by site-directed mutagenesis. Proc. Natl. Acad. Sci. USA 85:9273-9277.*

A. Ashkenazi et al., "Mapping the CD4 Binding Site for Human Immunodeficiency Virus by Alanine-Scanning Mutagenesis," *Proc. Natl. Acad. Sci. USA*, vol. 87, Sep. 1990, pp. 7150-7154.

J. Banerji et al., "A Lymphocyte-Specific Cellular Enhancer is Located Downstream of the Joining Region in Immunoglobulin Heavy Chain Genes," *Cell*, vol. 33, Jul. 1983, pp. 729-740.

F. Barré-Sinoussi et al. with L. Montagier, "Isolation of a T-Lymphotropic Retrovirus from a Patient at Risk for Acquired Immune Deficiency Syndrome (AIDS)," *Science*, 220, 1983, pp. 868-870.

R.S. Basch et al., "Expression of CD4 by Human Megakaryocytes," *Proc. Natl. Acad. Sci. USA*, vol. 87, Oct. 1990, pp. 8085-8089.

M.H. Brodsky et al., "Analysis of the Site in CD4 that Binds to the HIV Envelope Glycoprotein," *J. Immunol.*, vol. 144, No. 8, Apr. 15, 1990, pp. 3078-3086.

D.J. Capon et al., "Designing CD4 Immunoadhesins for AIDS Therapy," *Nature*, vol. 337, Feb. 9, 1989, pp. 525-531.

B. Castro et al., "Reactifs de Couplage Peptidique IV (1)—L'Hexafluorophosphate de Benzotriazolyl N-Oxytrisdimethylamino Phosphonium (B.O.P.)," *Tetrahedron Letters*, No. 14, 1975, pp. 1219-1222.

T.M. Chang et al., "Artificial Hybrid Protein Containing a Toxic Protein Fragment and a Cell Membrane Receptor-Binding Moiety in a Disulfide Conjugate," *J. Biol. Chem.*, vol. 252, No. 4, Feb. 25, 1977, pp. 1515-1522.

J. Chin, "Current and Future Dimensions of the HIV/AIDS Pandemic in Women and Children," *The Lancet*, vol. 336, Jul. 28, 1990, pp. 221-224.

S.N. Cohen et al., "Nonchromosomal Antibiotic Resistance in Bacteria: Genetic Transformation of *Escherichia coli* by R-Factor DNA," *Proc. Nat. Acad. Sci. USA*, vol. 69, No. 8, Aug. 1972, pp. 2110-2114.

D.B. Cawley et al., "Epidermal Growth Factor-Toxin A Chain Conjugates: EGF-Ricin A is a Potent Toxin While EGF-Diphtheria Fragment A is Nontoxic," *Cell*, vol. 22, Nov. 1980 (Part 2), pp. 563-570.

E.S. Daar et al., "High Concentrations of Recombinant Soluble CD4 are Required to Neutralize Primary Human Immunodeficiency Virus Type 1 Isolates," *Proc. Natl. Acad. Sci. USA*, vol. 87, Sep. 1990, pp. 6574-6578.

A.G. Dalgleish et al., "The CD4 (T4) Antigen is an Essential Component of the Receptor for the AIDS Retrovirus," *Nature*, vol. 312 20/27, Dec. 1984, pp. 763-767.

K.C. Deen et al., "A Soluble Form of CD4 (T4) Protein Inhibits AIDS Virus Infection," *Nature*, vol. 331, Jan. 7, 1988, pp. 82-84.

P.H. Duesberg, "AIDS Epidemiology: Inconsistencies with Human Immunodeficiency Virus and with Infectious Disease," *Proc. Natl. Acad. Sci. USA*, vol. 88, Feb. 1991, pp. 1575-1579.

A. Ehrnst et al., "HIV in Pregnant Women and Their Offspring: Evidence for Late Transmission," *The Lancet*, vol. 338, Jul. 27, 1991, pp. 203-207.

H. Okayama et al., "A cDNA Cloning Vector that Permits Expression of cDNA Inserts in Mammalian Cells," *Mol. Cell. Biol.*, Feb. 1983, pp. 280-289.

P.A. Orlandi et al., "Characterization of the 175-Kilodalton Erythrocyte Binding Antigen of *Plasmodium falciparum*," *Mol. Biochem. Parasitol.*, vol. 40, 1990, pp. 285-294.

G. Pasvol et al., "Inhibition of Malarial Parasite Invasion by Monoclonal Antibodies Against Glycophorin A Correlates with Reduction in Red Cell Membrane Deformability," *Blood*, vol. 74, No. 5, Oct. 1989, pp. 1836-1843.

R. Pearlman et al., "Pharmaceutics of Protein Drugs," *J. Pharm. Pharmacol.*, 44 (Suppl. 1), 1992, pp. 178-185.

M.E. Perkins et al., "Sialic Acid-Dependent Binding of *Plasmodium falciparum* Merozoite Surface Antigen Pf200, to Human Erythrocytes," *J. Immunol.*, vol. 141, No. 9, Nov. 1, 1988, pp. 3190-3196.

M.E. Perkins, "Surface Proteins of *Plasmodium falciparum* Merozoites Binding to the Erythrocyte Receptor, Glycophorin," *J. Exp. Med.*, vol. 160, Sep. 1984, pp. 788-798.

M.G. Peterson et al., "Variation in the Precursor to the Major Merozoite Surface Antigens of *Plasmodium falciparum*," *Mol. Biochem. Parasitol.*, vol. 27, 1988, pp. 291-302.

J.V. Ravetch et al., "Isolation of the Gene for a Glycophorin-Binding Protein Implicated in Erythrocyte Invasion by a Malaria Parasite," *Science*, vol. 227, Mar. 29, 1985, pp. 1593-1597.

P.J. Southern et al., "Tranformation of Mammalian Cells to Antibiotic Resistance with a Bacterial Gene Under Control of the SV40 Early Region Promoter," *J. Mol. Appl. Genet.*, vol. 1, No. 4, 1982, pp. 327-341.

B. Sugden et al., "A Vector that Replicates as a Plasmid and can be Efficiently Selected in B-Lymphoblasts Transformed by Epstein-Barr Virus," *Mol. Cell. Biol.*, vol. 5, No. 2, Feb. 1985, pp. 410-413.

R.P. Taylor et al., "Use of Heteropolymeric Monoclonal Antibodies to Attach Antigens to the C3b Receptor of Human Erythrocytes: A Potential Therapeutic Treatment," *Proc. Natl. Acad. Sci. USA*, vol. 88, 1991, pp. 3305-3309.

A. Traunecker et al., "Soluble CD4 Molecules Neutralize Human Immunodeficiency Virus Type 1," *Nature*, vol. 331, Jan. 7, 1988, pp. 84-86.

T. Triglia et al., "Large Fragments of *Plasmodium falciparum* DNA can be Stable When Cloned in Yeast Artificial Chromosomes," *Mol. Biochem. Parasitol.*, 44, 1991, pp. 207-212.

G. Tschumper et al., "Sequence of a Yeast DNA Fragment Containing a Chromosomal Replicator and the TRP1 Gene," *Gene*, vol. 10, 1980, pp. 157-166.

J. Wang et al., "Atomic Structure of a Fragment of Human CD4 Containing Two Immunoglobulin-Like Domains," *Nature*, vol. 348, Nov. 29, 1990, pp. 411-418.

X. Fang et al., "Cloning of the *Plasmodium vivax* Duffy Receptor," *Mol. Biochem. Parasitol.*, vol. 44, 1991, pp. 125-132.

Royce, Rachel A. et al. New England Journal of Medicine. Apr. 10, 1997; pp. 1072-1078 "Current Concepts—Sexual Transmission of HIV".

Feinberg, Mark B. Lancet 1996, 348 pp. 239-246 "Changing the Natural History of HIV Disease".

Ng, T.T.C., et al., Genitourinary-Medicine. 1996; 72(6) pp. 408-418 Molecular Immunopathogenesis of HIV Infections.

Erik De Clercq. Clinical Microbiology Review, Apr. 1995, pp. 200-239 "Anti-viral Therapy for Human Immunodeficiency Virus Infections".

G.B. Fields et al., "Solid Phase Peptide Synthesis Utilizing 9-Fluorenylmethoxycarbonyl Amino Acids," *Int. J. Peptide Protein Res.*, 35, 1990, pp. 161-214.

A. Furka et al., "General Method for Rapid Synthesis of Multicomponent Peptide Mixtures," *Int. J. Peptide Protein Res.*, 37, 1991, pp. 487-493.

M.J. Gait et al., "Rapid Synthesis of Oligodeoxyribonucleotides VII. Solid Phase Synthesis of Oligodeoxyribonucleotides by a Continuous Flow Phosphotriester Method on a Kieselguhr-Polyamide Support," *Nucleic Acids Res.*, 0305-1048/82/1020-6243.

T.F. Osborne et al., "Transcription Control Region Within the Protein-Coding Portion of Adenovirus E1A Genes," *Mol. Cell. Biol.*, Jul. 1984, pp. 1293-1305.

S.P. Adams et al., "Hindered Dialkylamino Nucleoside Phosphite Reagents in the Synthesis of Two DNA 51-Mers," *J. Am. Chem. Soc.*, vol. 105, No. 3, 1983, pp. 661-663.

J. Arthos et al., "Identification of the Residues in Human CD4 Critical for the Binding of HIV," *Cell*, vol. 57, May 5, 1989, pp. 469-481.

W. Fiers et al., "Complete Nucleotide Sequence of SV40 DNA," *Nature*, vol. 273, May 11, 1978, pp. 113-120.

R.A. Fisher et al., "HIV Infection is Blocked in Vitro by Recombinant Soluble CD4," *Nature*, vol. 331, Jan. 7, 1988, pp. 76-78.

F. Ahmad et al., "The Denaturation of Ribonuclease A by Combinations of Urea and Salt Denaturants," *Mol. Biol.*, 131, 1979, pp. 607-617.

R.C. Gallo et al., "Isolation of Human T-Cell Leukemia Virus in Acquired Immune Deficiency Syndrome (AIDS)," *Science*, vol. 220, 1983, pp. 865-867.

P. Gruss et al., "Simian Virus 40 Tandem Repeated Sequences as an Element of the Early Promoter," *Proc. Natl. Acad. Sci. USA*, vol. 78, No. 2, Feb. 1981, pp. 943-947.

B. Hess et al., "Cooperation of Glycolytic Enzymes," *J. Adv. Enzyme Reg.*, 7, 1968, pp. 149-167.

R.A. Hitzeman et al., "Isolation and Characterization of the Yeast 3-Phosphoglycerokinase Gene (PGK) by an Immunological Screening Technique," *J. Biol. Chem.*, vol. 255, No. 24, Dec. 25, 1980, pp. 12073-12080.

G.W. Hoffmann et al., "An Idiotypic Network Model of AIDS Immunopathogenesis," *Proc. Natl. Acad. Sci. USA*, vol. 88, Apr. 1991, pp. 3060-3064.

M.J. Holland et al., "Isolation and Identification of Yeast Messenger Ribonucleic Acids Coding for Enolase, Glyceraldehyde-3-Phosphate Dehydrogenase, and Phosphoglycerate Kinase," *J. Amer. Chem. Soc.*, vol. 17, No. 23, pp. 4900-4907. Publication date 1978.

E.H. Holt at al., "Erythrocyte Invasion by Two *Plasmodium falciparum* Isolates Differing in Sialic Acid Dependency in the Presence of Glycophorin A Antibodies," *Am. J. Trop. Med. Hyg.*, 40(3), 1989, pp. 245-251.

R. Hussey et al., "A Soluble CD4 Protein Selectively Inhibits HIV Replication and Syncytium Formation," *Nature*, vol. 331, Jan. 7, 1988, pp. 78-87.

M. Ivey-Hoyle at al., "Envelope Glycoproteins from Biologically Diverse Isolates of Immunodeficiency Viruses Have Widely Different Affinities for CD4," *Proc. Natl. Acad. Sci. USA*, vol. 88, Jan. 1991, pp. 512-516.

V.S. Kalyanaraman et al., "Evidence by Peptide Mapping that the Region CD4(81-92) is Involved in gp120/CD4 Interaction Leading to HIV Infection and HIV-Induced Syncytium Formation," *J. Immunol.*, vol. 145, No. 12, Dec. 15, 1990, pp. 4072-4078.

B. Kim Lee Sim et al., "Primary Structure of the 175K *Plasmodium falciparum* Erythrocyte Binding Antigen and Identification of a Peptide Which Elicits Antibodies that Inhibit Malaria Merozoite Invasion," *J. Cell Biol.*, vol. 111, Nov. 1990, pp. 1877-1884.

D. Klatzmann et al., "T-Lymphocyte T4 Molecule Behaves as the Receptor for Human Retrovirus LAV," *Nature*, vol. 312, 20/27, Dec. 1984, pp. 767-768.

D. Klatzmann et al., "HIV Infection: Facts and Hypotheses," *Immunology Today*, vol. 7, No. 10, 1986, pp. 291-296.

A.J. Kingsman et al., "Replication in *Saccharomyces cerevisiae* of Plasmid pBR313 Carrying DNA from the Yeast trpl Region," *Gene*, 7, 1979, pp. 141-152.

J. Kochan et al., "A Tandemly Repeated Sequence Determines the Binding Domain for an Erythrocyte Receptor Binding Protein of *P. falciparum*," *Cell*, vol. 44, Mar. 14, 1986, pp. 689-696.

J. Kost et al., "Responsive Polymer Systems for Controlled Delivery of Therapeutics," *TIBTECH*, vol. 10, Apr. 1992, pp. 127-131.

L.A. Laimins et al., "Host-Specific Activation of Transcription by Tandem Repeats from Simian Virus 40 and Moloney Murine Sarcoma Virus," *Proc. Natl. Acad. Sci. USA*, vol. 79, Nov. 1982, pp. 6453-6457.

L.A. Laimins et al., "Osmotic Control of *kdp* Operon Expression in *Escherichia coli*," *Proc. Natl. Acad. Sci. USA*, vol. 78, No. 1, Jan. 1981, pp. 464-468.

M. Lusky et al., "Bovine Papilloma Virus Contains an Activator of Gene Expression at the Distal End of the Early Transcription Unit," *Mol. Cell. Biol.*, vol. 3, No. 6, Jun. 1983, pp. 1108-1122.

P.J. Maddon et al., "The Isolation and Nucleotide Sequence of a cDNA Encoding the T Cell Surface Protein T4: A New Member of the Immunoglobulin Gene Family," *Cell*, vol. 42, Aug. 1985, pp. 93-104.

P.J. Maddon et al., "The T4 Gene Encodes the AIDS Virus Receptor and is Expressed in the Immune System and the Brain," *Cell*, vol. 47, Nov. 7, 1986, pp. 333-348.

P.J. Maddon et al., "Structure and Expression of the Human and Mouse T4 Genes," *Proc. Natl. Acad. Sci. USA*, vol. 84, Dec. 1987, pp. 9155-9159.

M.D. Matteucci et al., "The Synthesis of Oligodeoxypyrimidines on a Polymer Support," *Tetrahedron Letters*, vol. 21, pp. 719-722.

H.W.D. Matthes et al., "Simultaneous Rapid Chemical Synthesis of Over One Hundred Oligonucleotides on a Microscale," *EMBO Journal*, vol. 3, No. 4, 1984, pp. 801-805.

J.S. McDougal et al., "Cellular Tropism of the Human Retrovirus HTLV-III/LAV," *J. Immunol.*, vol. 135, No. 5, Nov. 1985, pp. 3151-3162.

J.S. McDougal et al., "Binding of the Human Retrovirus HTLV-III/LAV/ARV/HIV to the CD4 (T4) Molecule: Conformation Dependence, Epitope Mapping, Antibody Inhibition, and Potential for Idiotypic Mimicry," *J. Immunol.*, vol. 137, No. 9, Nov. 1, 1986, pp. 2937-2944.

J.P. Moore, "Simple Methods for Monitoring HIV-1 and HIV-2 gp120 Binding to Soluble CD4 by Enzyme-Linked Immunosorbent Assay: HIV-2 has a 25-Fold Lower Affinity than HIV-1 for Soluble CD4," *AIDS* vol. 4, No. 4, 1990, pp. 297-305.

R.A. Nelson, Jr., "The Immune-Adherence Phenomenon," *Proc. Roy. Soc. Med.*, vol. 49, Oct. 18, 1955, pp. 55-58.

D. Nolte at al., "A *Plasmodium falciparum* Blood Stage Antigen Highly Homologous to the Glycophorin Binding Protein GBP," *Mol. Biochem. Parasitol.*, vol. 49, 1991, pp. 253-264.

L.F. Novick et al., "HIV Seroprevalence in Newborns in New York State," *JAMA*, vol. 261, No. 12, Mar. 24/31, 1989, pp. 1745-1750.

\* cited by examiner

Fig 1(a) The binding of virus to red cells.

Fig 1(b) Vaccine formation using host derived virus

FUSION PROTEINS COMPRISING CD4 AND THE MALARIA PARASITE MEROZOITE GLYCOPHORIN BINDING PROTEIN 130 (GBP-130)

FIELD OF INVENTION

The field of this invention relates to protein molecules in particular hybrid protein molecules for the prevention of treatment of human beings afflicted with AIDS and diseases caused by Human Immuno Deficiency Viruses especially types 1 and 2; and other blood borne pathogens.

BACKGROUND ART

The AIDS syndrome is widely believed by the majority of Scientists (with a few exceptions) to be the end result of infection with Human Immuno Deficiency Virus type 1 or 2. Despite available treatment, on diagnosis of AIDS, life expectancy is short and death occurs usually within two years—death resulting from overwhelming infection and/or neoplastic diseases provoked by a profound immuno deficiency. The causative agent of this condition the HIV virus was proposed by Montagnier L and by Barre-Sinoussi F et al 1983, Science 220, 868-870 and slightly later by Galio R et al 1983, Science 220 865-867.

The accepted view of most Scientists is that this virus is necessary at least in part for production of this fatal Immuno Deficiency Syndrome. One notable exception to this belief is Deusberg P H who champions the minority view that AIDS is not caused by the Human Immuno Deficiency Virus and that it is not transmissible; Deusberg P H Proceedings National Acad Sci USA Vol 88, 1575-1579, February 1991. Regardless of the merits of this contradictory opinion and academic debate, work continues to find methods of combating the HIV virus and removing its presence from infected humans. Since the discovery of the HIV agent in the early 1980's screening of the worlds population has demonstrated that the HIV/AIDS pandemic is much worse than previously imagined. Evidence suggests that the impact of the disease will fall on disadvantaged women and children living in deprived urban areas or in sub-Saharan Africa or the Third World. It is estimated that 10 million persons will contract this condition before the year 2000 Chin J. Lancet 1990; 336: 221-224. Transmission of this virus to newborns from infected mothers remains a growing problem. At the present time in Africa, there are at least 2.5 million infected females who have given birth to an estimated 0.5 million infected infants. Disadvantaged urban areas in the developed world such as areas of New York associated with high rates of drug use have also shown high sero-positivity rates of HIV among neonates ie 2.2% compared with an overall sero-positivity of 1.25% among neonates in that city. NOVAK, Journal of America Medical Association 1989:261:1745-1750. The social and economic costs of this epidemic are likely to overburden the resources of health care providers and remains a growing area of concern. Our understanding of the timing of maternal to fetal transmission of HIV has been greatly improved by the study of Ehrnst A et al Lancet, 1981; 338: 203-207. He demonstrated effectively that the virus is transmitted vertically at the time of or close to delivery. Despite high viral titre levels during pregnancy it seems that the mixing of maternal and fetal blood at time of delivery is the most important mode of transmission from mother to fetus. In other contexts viral titre levels are directly related to disease severity; studies by Ho D D "Quantitation of Human Immuno Deficiency Virus type 1 in the blood of infected persons." New England Journal of Medicine 1989; 1621-1625 and the study by Combes R W et al "Plasma Vireama in Human Immuno Deficiency Infections" New England Journal of Medicine 1989; 321: 1626-1631. Both these studies have demonstrated rising levels of plasma vireama throughout the course of HIV and have suggested that high viral titres are associated both with the degree of immuno suppression, the presence or absence of symptoms and the likelihood of transmission to others. It has been shown that in the early stages of infection, viral titre levels measure 50 virus particles per ml rising to 10-50,000 virus particles per ml or more at the onset of AIDS.

In addition to the offspring of infected mothers, other large groups of the population are at risk or believe themselves to be at risk from the infection, especially homosexuals, drug addicts, persons receiving blood transfusions and health care workers. In the case of health care workers, the risk from a health care procedure carried out on infected persons is likely to be very low and is presently estimated to range of 0.3%-0.5% following needlesticks with an infected needle or surgical instrument. Operating room personnel frequently exposed to needlestick and other injuries are especially concerned at the present time. 8This concern is most marked among Orthopaedic Surgeons who in addition to needlestick injuries are liable to suffer abrasions or even transfixion of a digit with steel wires, pins and the like. So great is the concern that chain-male gloves have been devised to protect staff from inadvertent needlestick injuries. Disadvantages are apparent with barrier methods in relation to HIV prevention. In particular, increased costs—it is known that the dry goods budget of many hospitals has increased considerably following the onset of this epidemic. A second disadvantage is the loss of tactile sensation, making operative procedures more difficult and time consuming. A further problem is the difficulty in attracting and keeping staff in high risk areas who report psychological stress on their part or the part of their spouses, resulting from risk either real or imagined, particularly following needlesticks. A further area of concern is the safety of blood transfusions and the blood supply both in the US and elsewhere. To prevent repeating the iatrogenic infection of large numbers such as haemophiliacs with infected pooled factor 8, there has been a growing awareness of the need to take additional precautions with whole blood and blood product transfusion. The mainstay of transfusion safety remains screening, however no amount of screening can guarantee the safety of a blood transfusion or a blood derived product. Accordingly many workers have devised different methods to treat blood for donation. One is directed to the methods of Sieber U.S. Pat. No. 4,915,683 who discloses for example photosensatising agents useful to neutralise viruses and other pathogens in blood for transfusion. This approach and other similar methods is non specific however and requires an irradiating component in addition to a chemical means of treatment.

The present disclosure provides a means of improving the safety of blood products in one step.

The mechanism of HIV infection involves the binding of viral GP120 or envelope peptide to the CD4 peptide molecule. The CD4 protein is a 433 amino acid transmembrane glycoprotein which is found predominantly of the surface of T4 helper cells. It is also found on the surface of the mega karyocytes, monocytes, macrophages and other cells.

The CD4 molecule has three parts: an extracellular part which is divided into 4 variable domains V1 being responsible for the binding of HIV GP120; a short transmembrane region and an intracellular domain.

The CD4 molecule is part of the immunoglobulin super family. That CD4 was the receptor for the virus was shown by Dalglaoise et al 1984. "The CD4 antigen is an essential component of the receptor for the AIDS retrovirus" Nature: 212: 763-766. Also Madden P J Dalglaoise A G McDougall J S et al "The T4 gene encloses the AIDS virus receptor and is expressed in the immune system and the brain" Cell: 47, 333-348.

Maddon P et al Cell: Vol 47, 333-348 have shown that transformed mouse cells expressing the CD4 molecule possess the capabilities of binding the HIV virus though lack the ability to support the HIV infection at a cytoplasmic level. Debate continues within the art as to the precise binding site of GP120 with the CD4 molecule. Arthus et al Cell: Vol 57, 469-491 May 5, 1989 proposes that the binding site is contained at least within the first 106 amino acids of the CD4 molecule ie the V1 domain. He bases his assumption on substitute mutants and binding analysis with soluble truncated proteins demonstrating a high binding affinity solely within the first 106 amino acids of the CD4 molecule. Substitution studies led to the notion that the primary binding site on the CD4 molecule lay between amino acids 41-55.

Mizukani et al Proc Nat Acad Sci USA 85; 9273 (1988) and Arthus 1989 "Identification of the residues in human CD4 critical for the binding of HIV" Cell 57; 469 believes that the folded structures of the CD4 molecule brings other amino acids into play. Areas likely to be important in vital CD4 binding are reported to lie between amino acids 41-47 amino acids 16-49, 31-63 and 74-94 of the CD4 molecule.

The remarkable specificity of the virus for the CD4 molecule has lead to the attempts by many workers to utilise CD4 based peptides as therapeutic agents. The binding affinity for the GP120 with CD4 lies in the region of 3 nM. Many efforts have been made to utilise this high specificity.

In the case of HIV 2, the affinity is 20-25 fold less, however the binding strength as described is such that even a 25 fold reduction of affinity would not reduce the usefulness of therapeutic molecules based on CD4 and for that reason the binding reaction between GP120 and CD4 remains a logical target for anti HIV pharmaceuticals.

However the nature of the molecule means that a linear peptide will be unlikely to be successful in a therapeutic context.

Brodsky et al Immunology Vol 144, 3078-3086 Apr. 15, 1990 No 8 suggests that CD4 based therapeutic molecules should contain amino acids at least from the first 117 amino acids of the CD4 sequence.

Moore J P AIDS 1990, 4: 297-3-5 believes that the CD4 GP120 binding reaction is the one step this virus cannot afford to change by mutation to any appreciable extent.

Accordingly, attempts have been made to use recombinant CD4 peptides as therapeutic agents.

Fisher R et al Nature Vol 331, 7 Jan. 1989, "HIV Infection is blocked in vitro by recombinant soluble CD4" reported the use of recombinant soluble CD4 peptides that showed viral blocking activity in vitro. Hussey R et al "A Soluble CD4 protein selectivity inhibits HIV replications and Syncitium formation" Nature 331, 7 Jan. 1989, reported encouragingly that Syncitium formation could be blocked in vitro by the same CD4 based soluble peptides; and Dean et al "Soluble CD4 protein inhibits HIV virus infection" Nature 331, 7 Jan. 1989: A Traunecker et al "Soluble CD4 molecules neutralise Human Immuno Deficiency Virus type 1", also Nature Vol 331, 7 Jan. 1989 encouragingly reports that CD4 peptides may be used as therapeutic agents. The euphoria provided initially by these experiments was short lived.

Problems emerged, in particular the rapid clearance of recombinant soluble CD4 or sCD4 from the blood stream and secondly the existence of multiple binding sites on the virus.

It is known that the virus contains no less than a 72 GP120 molecules projecting from its surface. Therefore to fully neutralise a virus particle it would be necessary to combine recombinant soluble CD4 peptides or peptide based molecules with all 72 of the GP120 molecules the kinetics of this event are unfavourable. The present disclosure provides means to overcome both of these problems.

Further discouragement was provided by Eric Daar et al. Proc Nat Acad Sci USA Vol 87, 6574-6578. "High concentrations of recombinant SCD4 are required to neutralise primary immuno deficiency type 1 isolates." This report based on the treatment of 45 patients shows that soluble CD4 peptides failed to consistently reduce HIV titres and further suggests a reason for the failure being lower GP120-sCD4 affinities than being reported in vitro. Daar suggests that mutant strains possessing lower CD4 affinity than the strains used in laboratory testing may be responsible for the failure of the agents.

The present disclosure proposes that clinical disappointment with the T4 agents, such as disclosed in PCT WO89/019140 relates more to the short half life of the peptides in plasma and to the fact that 72 binding sites exist on a single virus, rather than due to lack of affinity between the agent and the virus itself. So great is the affinity between CD4 molecule and the GP120 molecule that even affinities 1000 fold less than those seen in vitro should be pharmaceutically effective.

Despite the failure of unmodified soluble CD4 as a HIV therapy, other workers have advanced alternatives in the hope of utilising the GP120-CD4 interaction. Examples of some of these alternatives are fusion peptides where a CD4 component is fused to another peptide having a different function.

Capon D J et al disclosed the use of CD4 fused to the FC component of the human Igh antibodies. The objective being to mobilise the compliment system and thereby destroy the virus particle by the compliment cascade. Capon refers to these new molecules as immuno adhesives. A possible disadvantage associated with this approach is the necessity of a fully functional compliment system, unlikely to the case in advanced HIV infections. See Capon et al "Designing CD4 Immunoadhesins for AIDS Therapy" Nature Vol 337.

The molecular machines of the present disclosure do not require a functional immune system and may be effective in cases where no immune function exists.

At the present time the main stay of treatment relies of the substance Azidothymine or AZT, this substance acts on the HIV enzyme reverse transcriptase.

An increasing number of patients and earlier in their illness are receiving treatment with AZT, however tolerance of this drug can be a problem. AZT is known to be lymphotoxic and is additionally associated with substantial anaemia. Haemato toxicity appears to be major limiting factor in the use of AZT in the treatment of ARC and AIDS Richman et al "The toxicity of the Azidothymine", New England of Medicine, 317; p 192-197, 1987. So profound is the anaemia provoked by this agent that many patients require frequent blood transfusions or treatment with Epogen (R), a novel genetically engineered erythropotein. The molecular machines of the present disclosure may be used in combination with AZT or other treatments and will augment the effectiveness of blood transfusions given to patients receiving AZT who are suffering from severe anaemia. Other agents acting on the reverse transcriptase such as DDC or DDI suffer high side effect profiles also and are toxic compounds in their own right. Equally, agents acting at other sites such as glycosylation are known to exhibit severe toxic effects on the host.

The agents of the present disclosures are anticipated to have lower toxic effects on the host than existing treatment modalities.

The agents may be used alone or in combination with existing treatments.

So great is the side effect problem of anti-AIDS therapeutics many feel it is likely that no one agent will be successful in combating this disease. One is directed to Fisher World Patent WO 89/11860 for a discussion of combination therapy.

More recently Taylor R P in Proceedings National Acad Science 88, p 3305-3309 refocused our attention on the work of Nelson published in 1950's who some years ago proposed an immune function for the red cells. Red cells (erythrocytes) are often considered to have only oxygen carrying and acid base balancing functions in the blood stream. According to Nelson red cells have additional immune functions. In particular Nelson proposed that opsonised antigens ie antigens whose surfaces were bound to compliment derived peptides could be fused to the compliment 1 receptor molecule (CR1) on the red cell surface. By fusing a virus or bacterium to the red cell surface in this way the virus or antigen becomes bound to the red cell surface in the manner of a barnacle bound to the surface of a ship.

A virus immobilised in this way would be harmless and be carried around the circulation on the red cell surface to await final phagocytosis and digestion at the end of the red cells life (usually 120 days from formation). It is thought that many antigens and pathogens are cleared from circulation by this mechanism rather than by direct phagocytosis and the like so frequently discussed in immunology texts. Accordingly, Taylor R P proposed a technique to utilise this long forgotten mechanism. He suggested the use of hybrid antibodies capable of binding both to the HIV virus and to the compliment 1 receptor molecule of the red cell surface. The adherence of virus particles to the red cell surface membrane in this way would clear the blood stream of free virus particles and free GP120. Thereby attempting to achieve Nelson's proposition that one day red blood cells could be harnessed to rid mankind of infection.

The peptide machines of the present disclosure provide totally different mechanisms to achieve Nelson's dream ie to bring about the binding of HIV virus particles to the red cell surface membrane.

The agents of the present disclosure carry the additional advantage in that antibodies to the compliment peptides and red cell surface CR1 are not a feature. This would be an advantage in that the risk of destabilising an already unbalanced immune system is not expected to be a feature of the molecules of the present disclosure.

The Third World or underdeveloped world is no stranger to epidemics and has prior to the development of AIDS and HIV been ravaged by infectious disease: the most serious on a global scale is probably malaria. Various forms of importance to humans are *Plasmodium Falciparum, Plasmodium Vivax, Plasmodium Ovale. Plasmodium Malariae*. This serious parasite infests red blood cells. The life cycle is complex and consists in part of a short life cycle in the salivary gland of mosquitoes. Following innoculation into a human being, the malaria organism migrates to the liver and to the red blood cell. It multiplies forming further merozoites. Merozoites may then proceed to infect other red blood cells, or may find their way into another mosquito where they replicate in the mosquito salivary gland and later proceed to infect another human being.

The course of malaria is a variable one and may be characterised by a short acute illness which can bring death in a matter of hours; or a longer more chronic illness associated with debility and anaemia. Other forms of malaria infect animals such as *plasmodium* Knowlesi which is known to infect the Rhesus monkey; and many other zooanotic forms.

The preferred location for the malaria parasite is within the red cells of the infected host and for much of its life span it lives intracellularly protected from the host immune system.

Merozoites are thought to spend but a brief period free in the circulation. Accordingly, considerable research efforts have been expended to discover the means whereby the merozoite forms of the parasite gains attachment and gains entry into the human red cell.

Margaret E Perkins Journal Experimental Medicine 160 September 1984, 788-798 is responsible for the formulation of a relationship between the *Plasmodium Falciparum* glycophorin binding molecule and glycophorin A and B two silao glycoproteins found on the surface of red cells.

More laterally, Holt and Perkins et al American Journal Tropical Medicine Hygiene 1989, p 245-251 disclose species and stain variations of *Plasmodium Falciparum* wherein some strains of the organism exhibit preference for sialo glycoproteins glycophorins A, B and C; and also demonstrated was the varying requirements for the N-acetyl-neuramic acid residues (NeuNac).

The glycophorin A molecule is a highly glycolated peptide. Pasvol has suggested that glycophorin binding peptide binds to the region of glycophorin close to the lipid bi-layer. Pasvol G et al "Inhibition of Malaria Parasite Invasion by Monoclonical antibodies against glycophorin A correlates with a reduction in red cell membrane deformality." Blood 74, No 5, October 1985, 1836-1843. Debate continues within the literature as to the requirement for sialic acid on the glycophorin molecule to effect invasion by merozoites.

Some strains of malaria are totally dependent on normally sialated glycophorin A to gain entry into the red cell, whereas other strains seem to be independent of sialic acid. See Mitchell et al 67, No 5 May 1986 1519-1521. Perkins and Roco in Journal of Immunology, 88, Vol 141, 3190-3196 No 9, again stress the importance of sialic acid where normally silated glycophorin is necessary to achieve successful binding of merozoite peptides, in particular to pf200.

For several years a peptide called the glycophorin binding protein was believed to be the primary peptide responsible for binding merozoites to erythrocytes. A gene coding for GBP was isolated by M Ravetch and Kochan J and disclosed in Science Vol 227, p 1593-1596.29 Mar. 1985 and incorporated herein fully by reference.

GBP 130 is characterised by a tandem repeated sequence believed to be the site of erythrocyte binding, "A tandem repeated sequence determines the binding domatin for an erythrocyte receptor binding protein of *plasmodium falciparum*". Kochan J, Perkins M and Ravetch J Cell, Vol 44, 689-696 March 1986. See FIG. 2 p 691 which also discloses the full sequences and genetic code of the GBP 130 molecule and is incorporated fully herein by reference.

Other workers have challenged the supremacy of the GBP 130 as the primary binding molecule of the malaria merozoite, Orlandi P; Kim Lee Sim et al Molecular and Biochemical Parasitology, 40 (1990) 285-294 "Characterisation of the 175 kilodalton erythrocyte binding antigen of *plasmodium falciparum*" suggested a different peptide, the EBA 175 molecule, as being responsible for merozoite binding or at least playing some role therein. The EBA 175 molecule like the GBP 130 molecule has an affinity for the red blood cell surface and binds thereto.

It is known that the EBA 175 molecule has an affinity for oligosaccharides which are found on the surface of the red cell molecule. However a problem arises in that the EBA 175 molecule does not bind effectively with the malaria merozoite parasite. Therefore it is thought that the EBA 175 serves a function as a bridge. This disclosure proposes an alternative mechanism in that the EBA 175 molecule is responsible for bringing the merozoite close to the erythrocyte membrane surface, thereafter GBP 130 drags the merozoite closer still by binding with the base of the glycophorin A peptide; thus bringing the lipid bilayer of the malaria parasite into approximation with the lipid bilayer of the red cell membrane and thereby allowing the incorporation of the parasite into the erythrocyte itself. This disclosure suggests the merozoite is winched into the RBC cytoplasm.

The genetic sequence and the peptide sequence of EBA 175 was disclosed by Kim Lee Sim. Orlandi P et al "Primary structure of the 175 K *plasmodium falciparum* erythrocyte binding antigen and identification of a peptide which elicits antibodies that inhibit malaria merozoite invasion" See J Cell Biology Vol 111 (1990) p 1877-1884 FIG. 2 of P 1880 for the sequence of amino acids and DNA sequence.

To further complicate the picture Dagmar Nolte et al described two close relatives of the glycophorin binding peptide 130 molecules which they call GBPH or glycophorin binding peptide homologues. These molecules like the GBP molecule display several tandem repeat sequences and a high affinity for the erythrocyte surface membrane surface peptides. It has been proposed by Nolte and co-workers that it is the GBPH molecule and not the GBP molecule that is responsible for erythrocyte binding of the parasite in that the GBP molecule is released as an immunogenic decoy to distract the immune system from the real binding peptide the GBPH.

The nucleotide sequence and amino acid sequence of one form of the peptide GPBH is disclosed by Dagmar Nolte et al in the Journal of Molecular and Biochemical Parasitology 49, (1991) p 253-264 see FIG. 2 of p 257 incorporated herein fully by reference. See also FIG. 3 of p 258 the same journal and paper which lists a comparison between GBP 130 and GBPH. Binding and entry of merozoites into RBC's probably involves several peptides or several alternatives as fail safes for the organism.

The picture is further complicated by other research notably by Peterson Gregory who proposes PMMSA (Pre major merozoite surface antigen) as being responsible for erythrocyte binding either in this state or following fragmentation into smaller fragments. The genetic sequence and the peptide sequence of the PMMSA molecule is given in the Journal of Molecular and Biochemical Parasitology 27 (1988) 291-302 see FIG. 3 of P 294 and 295 Peterson G et al, and is incorporated fully herein by reference.

Erythrocyte binding using different peptides and surface molecules is exhibited by other species of the malaria parasite in particular the *Plasmodium Vivax* organism. This organism can infect only persons expressing the Duffy marker. The Duffy antigen is a red cell surface marker and is one of many blood group markers and carried by a percentage of the population. Persons not expressing Duffy antigens are therefore immune from infection by *Plasmodium Vivax*. The *Plasmodium Vivax* merozoite expresses a Duffy binding receptor molecule the *P. vivax* Duffy receptor, cloned and sequenced by Xiangdang Fang and disclosed in Molecular and Biochemical Parasitology 44 (1991) p 125-132 see especially FIG. 1 of p 127 for the genetic sequence and amino acid sequence. Similar to *Plasmodium Vivax* is Pladmodium Knowlesi which also uses the Duffy antigen. This organism parasitises Rhesus monkeys. Also in the same Journal, same figure, same page is listed the genetic sequence of *Plasmodium* Knowlesi Duffy receptor molecule which may find a use in the machines of the present disclosure.

When developing therapeutic agents directed against the malaria parasite itself then it is the teachings of the art to identify the precise molecule responsible for merozoite binding in the clinical context. However, this disclosure teaches that where malaria peptides are to be employed as erythrocyte binding agents more generally then it is not important to identify the precise peptide the malaria organism uses to effect invasion, rather any malaria peptide capable of binding to an erythrocyte surface membrane may have a therapeutic use for the purposes of the machines of the present disclosure and also segments of such a peptide.

It is disclosed that the machines of the present invention consists of hybrid peptides formed by the fusion of malaria derived peptide sequences sufficient to exhibit erythrocyte membrane affinity fused to a CD4 derived peptide sequence sufficient to demonstrate affinity for the HIV virus. The restriction map and peptide sequence of the CD4 molecule are disclosed by Madden et al Proceedings National Acad Science USA 84; 1987 p 1955-1959 see especially FIGS. 1 and 2 incorporated herein fully by reference.

Also Madden et al Cell Vol 42, P 93-104 August 1985 especially FIG. 6 of P 97.

It will be appreciated that the CD4 peptide components will not be restricted to segments of the naturally occurring CD4 molecule. Also, the malaria derived peptide fragments may be any that are capable of binding to the red cell membrane and one is especially directed to those referenced herein before.

BRIEF SUMMARY

The present disclosure provides novel hybrid or fusion peptides having a minimum of two different peptide components possessing different functionality. One component, preferably the CD4 molecule or segment or derivative thereof which is capable of binding to an HIV virus is fused or joined to a malaria derived peptide or derivative or fragment thereof which is capable of binding to a red cell membrane. The fusion y peptide will in one aspect bind the free HIV virus to a red cell producing possible therapeutics benefits of:

a) reduced free virus in circulation;
b) reduced free GP120 in circulation;
c) reduced symptoms and infectivity, both generally and prior to delivery;
d) augmented therapeutic usefulness of blood transfusions;
e) greater safety of blood transfusions;
f) immune augmentation by novel vaccine effects;
g) usefulness as prophylaxis, eye drops for theatre staff; preparations, creams, lotions and foams for contraceptive use; preparations for exposed cuts or abrasions;
h) simpler safer and economic viral titre measurements;
i) preparation for cleaning surgical instruments.

It will be appreciated that more than the minimum two components may be used to form the fusion peptides mixed in any combination to produce more complex molecular machines without departing from the scope and spirit of the invention.

eg

```
       CD4   CD4              CD4    CD4
GBP ────┴──/──GBPH   or   GBP ──┴──/──EBA   or
          CD4 ──── EBA ──── GBP
``` or where A denotes a malaria fragment and B denotes a CD4 derived fragment and 'm' and 'n' are natural numbers, the disclosure contemplates in some aspects the hybrid molecules such as:—

Am Bn; (ABA)n
(AB)n; (BAB)m and the like which also fall with the scope and spirit of the present disclosure.

DESCRIPTION OF DRAWINGS

The FIGS. 1(a) and 1(b) are provided on Drawings sheet 1 of 1.

FIG. 1(a) depicts free HIV virus particles drawn to and immobilised on a red cell (RBC).

FIG. 1(b) depicts the formation of a novel vaccine within the host blood stream utilising HIV components (live virus) derived from the host rather than provided from external sources as would be usual; for vaccines.

DETAILED DISCLOSURE AND EXEMPLARY EMBODIMENTS

The molecular machines of the present disclosure are prepared by the conjugation of at least two separate components into a single larger molecular entity or conjugate peptide. A minimum of one HIV binding component is joined to a minimum of one RBC peptide. A minimum of one HIV binding component is joined to a minimum of one RBC binding component. The components may be joined directly or indirectly to a junctional sequence or cross linkers.

The simplest form of a molecular machine will consist of a HIV binding peptide and an RBC binding peptide fused by peptide bonds giving the following structure:

| HIV Binding Peptide | | RBC Binding Peptide |
|---|---|---|
| | Middle of molecule & site of fusion not critical | |

The functional areas of the machines are preferably situated towards either end. Therefore the middle of the molecule and the site of fusion is not critical.

It will be appreciated that the two components may be fused directly or an intervening segment or peptide sequence or linker be interposed between them. Such a segment could be any peptide sequence such as:

a) the junctional areas of the CD4 molecule;

b) the Fc segment of an immunoglobulin:

c) or any macromolecule or cross linker or part thereof.

The interposed segment may or may not retain functionally of its own but must not interfere with the function of HIV binding and RBC binding. The preferred HIV binding component is a CD4 peptide sequence all or part thereof retaining HIV binding. However, it will be apparent to the skilled artisan that a CD4 therapeutic agent such as CD4-Fc retaining a functional HIV binding moiety would also provide a suitable HIV binding component. In that event, the Fc fragment would become a spacer or peptide cross linker between the CD4 segment and the RBC binding peptide.

The alternative becomes:

| CD4 | SPACER PEPTIDE CROSS LINKER | RBC BINDING PEPTIDE |
|---|---|---|

It will be appreciated that the use of a CD4-Fc peptide or any CD4-P where P is a non-specific peptide sequence, in place of a simple CD4 peptide segment falls, within the scope and spirit of this invention regardless of whether the middle component retains functionality or not. One is directed to WO 89/02922 Genetech Danial J Capon for a description of immunoadehesions comprising eg CD4-Fc fusion peptides which may be used in place of CD4: and is incorporated fully herein by reference.

The envisaged mode of action of the therapeutic machines of the present disclosure is that one component of the molecular machines, the CD4 derived component will bind with the HIV virus GP120 molecule or free GP120 whilst the merozoite derived peptide segment will bind with the erythrocyte membrane surface. Either glycophorin A, B, C or to the Duffy antigen where a Duffy receptor peptide is used.

The outcome of this binding will be to immobilise the virus particle onto the surface of the red cell much like a barnacle to the surface of a ship, and thereby neutralise it.

Thereafter the virus will be carried around with the red cell harmlessly to await destruction by mechanisms such as phagocytosis.

It is likely that the peptides will have a long half life in vivo. It is known that merozoites have a predilection for young red cells rather than mature red cells. Therefore the problem of short half life seen with previous CD4 based therapies will be eliminated to a certain extent. The effect of this viral binding will be to sweep the circulation clear of free virus particles, reducing the victims infectiveness to others. The peptides of the present disclosure will find uses as molecules to be injected prior to surgery, molecules to be injected, prior to delivery, molecules to be mixed with blood transfusions (whole blood) to be given to AIDS victims thereby to improve the therapeutic effectiveness of tranfusions and molecules to reduce the high viral titre levels believed to be associated with symptomatic AIDS and molecules for prophylaxis generally.

A further benefit of the machines of the present disclosure is the possibility of incorporation of the virus into the red cell cytoplasm. It will be appreciated that although this step is not essential to the present disclosure, immobilisation being sufficient, nevertheless were a virus to attempt infection of a red cell such infection resulting in the dismantling of the virus outer coat and the incorporation of the virus RNA into the red cell cytoplasm this would be a completely wasted exercise from the viral point of view. Red cells lack a nucleus and a virus once incorporated into a red cell cytoplasm is immobilised and neutralised forever.

It is envisaged that normal dosage levels of a peptides of the present disclosure will range from 0.01 mg/kg to 10 mg/kg. The agents of the present disclosure may also find a use in diagnostic testing and viral titre quantification.

The molecular machines of the present disclosure may act beneficially in further ways.

The GP120 binding component (CD4 derived sequence) may bind the molecular machines to infected cells expressing GP120. Expression of GP120 by infected cells occurs prior to viral shedding The resultant complex.

infected Cell ———— surface GP120 ———— CD4 ———— malaria peptide may mobilise an immune reaction against the infected cell killing the infected cell thus preventing viral release.

Further were this immune response to be in the form of cellular immunity or continue in the absence of the molecular machines of the present disclosure, then the said machines would constitute a long awaited vaccine or immuno modulator against HIV.

It is known for instance that cellular immunity is highly desirable in combating HIV infection. It is known that HIV victims with enhanced cellular immunity live longer and remain symptom free for long periods.

The generation of a cellular immune response has been found to follow where an infection antigen (virus) has been ingested by a macrophage APC (antigen presenting cell). Live viruses are processed differently to non infectious particles by APC's. Live viral antigens are digested in the cytoplasm of the APC (cytoplasmic pathway) and digested particles presented on the APC surface in association with class 1 MHC markers provoke a cellular immune response (Whitton J L Oldstone M B A Class 1 MHC can present endogenous peptide to cytotoxic lymphocytes J Exp Med 1989 170: 1051-56). Accordingly the degradation of HIV (live virus) coated RBC's in the spleen or reticulo endothelial system could encourage a cellular immune response. By capturing endogenous live virus and by binding the said live virus to a cell destined for destruction by phogocytosis, the molecular machines of this invention provide a vaccine of a particularly novel variety in that:
1) the vaccine as administered contains no components derived from the pathogen target of the vaccine (no HIV component), eg rGP120;
2) the vaccine obtains its pathogen derived component direct from the host and modifies host produced live virus;
3) the red cell surface is incorporated into the final immunogenic construct.

It should be noted that the art teaches that vaccines should usually contain material derived from the target pathogen. This disclosure teaches vaccines which do not provide target pathogen-derived material in that the material derived from the target pathogen of the vaccine is provided later in the host. The precise mechanism for the generation of cellular immunity is not understood. It is a further unproven postulate of this disclosure that cellular immunity generally proceeds from the processing of pathogens bound to erythrocytes when the said pathogens are engulfed with their red cell symbiot in the liver, bone marrow or spleen. Possible proof of this hypothesis lie in the following facts:
1) the fact that splenectomy leads to a defect in cellular immunity;
2) the fact the splenectomy is beneficial in hypoimmune states such as ITP idiopathic thrombocytopaenic purpurpae.
3) The tact that cellular immunity is a delayed phenomenon which would be consistent in that the spleen must wait for RBC's with bound antigens to 'age' sufficiently before engulfing them.
The precise role of the spleen in the 'immune' system is not clearly understood.

However, although it is useful to speculate on the above hypothesis they are disclosed herein as notions worthy of further study, and not binding to the disclosure.

EXAMPLES OF CLINICAL MODE OF USE OF MOLECULAR MACHINES

Example 1 of Clinical Mode of Use

The molecular machines of the present disclosure in one aspect are prepared and packaged in lypholised form and stored in refridgerated conditions. The lypholised fusion peptides are reconstituted by means of injectable solvents such as injectable preparations of normal saline or dextrose 5% or the like together with buffers and other stabilising ingredients incorporated as necessary.

The reconstituted molecular machines (fusion peptides) are administered to patients by either the Direct or indirect method.

Direct method involves the intravenous or even intra muscular administration of the reconstituted injectable solution of the molecular machines of amounts usually not exceeding 1,000 mg of agent per ml. The agents may be infused slowly by means of an intravenous drip or when safe to do so or if necessary by bolus injection.

The slower administration rates provide more even mixing of agent with red cells therefore labelling many more red cells.

A disadvantage with targetting large numbers of red cells is the risk of haemolysis. But the advantage is longer half life of the agent. Bolus administration or rapid administration reduces haemolysis because fewer red cells are carrying the agents, however those fewer red cells will have a shorter plasma half life.

Indirect methods of administration envisage the mixing of the reconstituted agents with red cells outside the body. The agents may be added to blood transfusion units all or part prior to administration or the agents may be mixed with a quantity of the patients own blood. Ten mls of the patients own blood is mixed with citrated buffer and thereafter with the reconstituted molecular machines. A degree of mechanical agitation is provided. The treated blood is now reintroduced into a suitable vein, slowly at first to observe for untoward reactions.

The procedures above may be repeated until side effects such as haemolysis or idiosyncratic reactions prevent their further use. It is envisaged that the agent will be administered as courses of treatment on a 3 to 4 monthly basis.

It will be appreciated that the agents are not necessarily restricted to lypholised forms. It has recently been shown that following liquid storage recombinant peptides perform better than freeze dried preparations, in some cases this was demonstrated for IFN see Pearlamn and Tue Nguyen J Pharm Phamacol 1992, 44 (suppl 1): 178-185.

Example 2

The agents may be formulated in slow release forms allowing the gradual leaching of active peptide molecular machines over a time period. Examples of such methods are the incorporation of the agents into biodegradable polymers. Such polymers could be injected as subdermal 'rice grains' or form part of an intrauterine contraceptive device.

Intrauterine contraceptive devices (IUD'S) impregnated with the agents of the present disclosure would slowly leak the agents towards the cervix. Cerival erosions are known to be an area of major importance in women's vulnerability to AIDS. Indeed the heavier menses associated with IUD's would leach more of the peptides from the polymer and by targetting menstrual blood or on their own provide a useful degree of protection against the virus. Such a use would be very helpful in the Third World.

For a useful reference on polymer delivery systems see Kost J and Langer R Tibech April 1992 Vol 10, 127-131 incorporated fully herein by reference.

Example 3

The novel peptide agents of the present disclosure may by incorporated into creams and gels or foams for use as topical preparations. Such compositions may be used in conjunction with:

a) barrier contraceptives;

b) in place of existing lubricating agents or with lubricating agents generally

The said creams, gels or foams may also be used to dress wounds, cuts or open sores or as contraceptive agents or in conjunction with contraceptives especially barrier methods. In the case of HIV positive patients such sores would become reduced sources of infection for others.

In the case of medical personnel such creams, gels or foams and the like could render abrasions or cuts more protected against contamination by tree virus from patients. Such a mode of use as a prophylactic may be especially helpful for theatre personnel.

Example 4

The agents of the present disclosure are formulated into drops, especially eyedrops. During surgical operations eye splashes are a frequent occurrence. Theatre staff although strongly warned to use eye protection often fail to do so for reasons of discomfort, haste or carelessness. Existing eyewash preaprations do not contain specific anti-viral components. The present agents are formulated as surgical eyedrops or eye washes useful as emergency decontaminants of splashed eyes during operative procedures.

Examples of Clinical Use as Testing Agents

The Liquid Phase Use of Malaria Erythrocyte Binding Peptides Fused to CD4 in HIV Tests and Viral Titre Quantification A measured volume of blood or fluid to be assayed is mixed with a known quantity of molecular machines; usually 1 ml of sample blood with 20 ug of CD4-merozoite fusion peptides, following a period of incubation, agitating the sample so as to bring red cells into contact with the virus, the sample is further incubated with a fluorescent labelled anti HIV GP120, anti GP160 or anti GP41 antibody or cocktail thereof. Separation is carried out by centrifugation or filtration. After adequate washing of cells by appropriate buffer, cell fluorescence is measured in a cell sorter. The advantages of such a liquid phase HIV test are:

1) high specificity owing to the concentration of antigen in one small spot on a red cell, helping fluorescent contrast
2) ease of automation
3) quantification of viraemia. Up to now HIV viraemia has been difficult to quantity. Cheaper methods of viral quantification will assist in new drug development.

Examples of Methods of Manufacture

The fusion peptides of the present disclosure may be manufactured by a wide variety of manufacturing methods and strategies; which may be applied in various combinations.

Both the number and variety of suitable methods of manufacture are increasing rapidly at the present time and are widely known and practiced by persons skilled in the art. Accordingly in the interests of brevity reference will be made to some but by no means to all of the manufacturing methods suited to the present disclosure.

The various manufacturing methods may be combined in different combinations to form a final strategy. In one strategy the fusion peptides may be manufactured by means of the separate manufacture of components such as components A and B and subsequent fusion of A and B in vitro using various means eg by chemical linkers. Peptide sequences even greater than 150 amino acids long may be manufactured entirely synthetically in vitro. Accordingly where component A or B of the fusion peptide is less than 150 amino acids in length this component may be made synthetically as a single component. Where component A or B is very long component A or B may be manufactured synthetically in smaller fragments to be bonded chemically there after in vitro, the said bonding to be preferably peptide bonds and achieved by methods such as segment condensation or by other methods known to the art.

The two peptide components A and B may also be fused using chemical linkers or by disulphide bonds as disclosed by Chan et al 1977, J Bio Chem 252; 1515-1522. Miskimins et al 1979 Bio Chemi Biophys Ref Comune 1991; 143-151 discloses a fusion peptide formed using cystamine as the cross linking agent. Cawley et al 1980 Cell 22, 563-70 discloses the use or hetrobifunctional cross linking agents to form a hybrid molecule consisting of RICIN A joined to epidermal growth factor EGF. Other useful strategies for fusing peptide sequences employ linking groups such as the chelating agent DTPA. To facilitate the fusion of peptide sequences by means of chemical linking groups it may be helpful to fix one or both peptide sequences onto a solid substrate such as resin beads or polyacrylamide gel or cross linked polystyrine or other anchoring mority.

The recent art continues to provide new techniques for applying the Merrifield synthesis of peptides on a scaled up basis useful for the large scale manufacture ie of peptides such techniques are termed "scale up of solid phase peptide synthesis". Merrifield synthesis may be very suited to the tandem repeat segments of malaria derived peptide components. In the interests of brevity a full account of peptide synthesis will not be given which techniques are widely known and practiced by the skilled artisans but reference will be made to some more interesting or recent developments in peptide manufacture.

A recent development involves the use of a new anchoring moiety involving the bondying of (HYCRAM) (R) (Orpegen GMBh, Czernyring 22, D-6900 Heidelberg FRG) a 4-hydroxy-crotonoyl-amidomethyl group bonded to an aminomethyl-polyacrylamide gel via spacer molecules such as a B-alanaine or sarcosine or the like. Fmoc-amino acids can be linked to the HYCRAM (R) by esterification. Also any Boc-amino acid or any Ddz-amino acid 3,5-di methoxy phenyl-2-propyl-2-oxycarbanyl-amino acid salt may be bonded to the HYCRAM (R) anchor.

Synthesis then proceeds using the Boc-/benzyl, the Ddz-/t-butyl or the Fmoc-/t-butyl protocols as usual.

Detachment of the peptide from the HYCRAM (R) support employs palladium tatra-kis (triphynyl-phosphane) a catalyst in a suitable solvent such as 50% (v/v) dimethylsuphoxide with dimethyl formamide: N-methylpyrrolidine, tetrahydrofuran and water. Oxygen tetrahydrofuran must be excluded. Acceptor molecules, morpholine, dimedine or N,N'-di methylbarbiturate may be added to take up the allylic group.

The Ddz-/t-butyl amino acid protections are easier to cleave using with 1-5% (v/v) trifluoroacetic acid in dichloromethane a process taking 10 to 30 minutes or by means of the more environmental friendly acetic acid or dioxane containing 1% (w/v) HCL gas. The other useful protocol is the Fmoc-/t-butyl strategy. Cleavage of F moc can be achieved using 20-50% (v/v) piperidine/dimethyl formamide. Deprotection can be monitored in both cases photometrically. The activation of Boc-; Fmoc-; or Ddz-amino acid derivatives may employ the inexpensive (DCC) diclohexylcarbodiimide. Pre activation using HOBT (N-hydroxybenzotriazole) can be employed to form symmetric anyhydrides of protected amino acids or their esters. Other activating agents are the Castro Reagent or BOP; Benzotriazole-1-yl-oxy-tris (dimethyl amino) phosphonium hexa fluorophosphate; one is directed to CASTRO B et al (1957) Tetrahedron Lett 14, 1219; and TBTU the Knorr reagent, Benzotriazole-l-yl-oxy-l, 1,3,3-tetramethyluronium tetrafluoroborate one is directed to Knorr R et al (1989) Tetrahedron Lett 30, 1927. Fragment condensation can be achieved using the BOP or the TBTU reagent with HOBT in excess. Protected peptides may also be in excess, however solvents and excesses can often be recycled.

It will be appreciated that by blocking incomplete fragment condensations shorter by-products can be discriminated from the desired polypeptide. Using this system high purity polypeptides can be produced.

Monitoring of the production process will usually involve U.V. absorption techniques.

A typical production process involves either the separate synthesis of peptide sequences by their expression in suitable hosts, and their subsequent purification and fusion; or chemical synthesis such as on a solid substrate for example by the sequential addition of amino acid residues or peptide fragments which are protected, the protection of the amino acid residues as required and the subsequent reacting of the peptide chains with linking agents before removing the peptide chains from the said solid substrates and the final purification by the various means is such as reverese phase chromatography; or any combination of the above.

In the case of some of the exemplary embodiments it may be convenient to manufacture the fusion peptides by means of a fused gene. A fused gene is a genetic sequence which codes for both components of the hybrid component molecule. One is directed to Murphy U.S. Pat. No. 4,675,382 for a detailed disclosure of the use of fused genes in the manufacture of hybrid peptides having the components MSH or Melanocyte Stimulating Hormone fused to dipcheria A toxins.

Alternatively peptide fragments may be manufactured by DNA cloning and expression in suitable hosts and recovery with subsequent condensation in vitro.

Generally cloned sequences useful for the production of fusion peptides will have the transmembrane domain and the cytoplasmic domain sequences removed.

For a useful general description of DNA cloning and modular hydridization technology, one is directed to Mainiatis et al Molecular cloning, A Laboratory Manual, Cold Spring Harbour laboratory (See Second Edition 1989); and to Horvath et al An Automated DNA synthesiser employing Deoxynucleoide 3 phorphoramidites, methods in enzymology 154: 313-326, 1987. One is also directed to "Principles of Gene Manipulation an Introduction to Genetic Engineering" Old R W and Primrose S B Ed 4: Blackwell Scientific Publications ISBN 0-632-02608-1 incorporated fully herein by reference. DNA may be made by the chemical synthesis of DNA polymer fragments using phosphotriester, phosphite or phosphoramidite chemistry. For a description of solid phase techniques one is directed to Chemical and Enzymatic Synthesis of Gene Fragments—A Laboratory manual ed H G Gassen and L Lang, Verlag Chemiee, Weinheim 1982; and Gait M J et al Nucleic Acids Research 1982, 10, 6243; Spoat B S et al Tetrehedron Letters 1980, 21, 719: Matteuci M D et al J of American Chemical Society 1981, 103, 3185; Sinha N D et al Nucleic Acids Research 1984, 12, 4539; Adams S P et al J American Chemical Society 1983, 195; 661; and Matthes H W D et al Embro Journal 1984, 3, 801; and are incorporated herein fully by reference.

Reverse transceptase techniques may also be used to generate a complimentary c DNA strand by means of the reverse transcription of malaria parasite derived mRNA. Kits are available for this purpose.

The DNA fragments may be ligated by either blunt-ended or staggered-ended termini using restriction enzymes; digestion; filling in as required; and treatment with alkali and phosphatase for protection and subsequent ligation with suitable ligases.

Appropriate leader sequences may be chosen from the many available.

The cloning of the DNA sequences of the hybrid peptides of this invention may take place in prokaryotes such as *E coli* for example K12 strain 294 or *E coli* B or *E coli* X1776 by way of non limiting examples or by means of the polymerase chain reaction.

Subsequent expression of the hybrid peptides may take place in any host cell, but preferably mammalian host cells. Other useful cells are fungi, yeasts, insects and prokaryotes. Signals suited to the chosen host cell are chosen as appropriate, in the case of prokaryotes one can chose from a large group including alkaline phosphatase and the like.

Where prokaryotes are used to express the hybrid peptides, then they are transformed by an expression vector usually a plasmid such as PBR322 into which the DNA encoding the fusion peptide or fragment has been ligated such a plasmid will also feature suitable marker sequences, promoters and Shine-Dalgarno sequences may be chosen as appropriate.

A prokaryote host such as *E coli* may be transformed by treatment using a solution of $CaCl_2$ as described by Cohen et al PNAS 1973, 69; 2110 or by treatment with a solution comprising a mixture of RbCl. $Mncl_2$, potassium acetate and glycerol and then subsequently with 3-(N-morpholino)-propene-sulphonic acid and RbCl and glycerol.

One is directed to "DNA Cloning" Vol II D M Glover ed, IRL Press Ltd 1985 for a description of transforming techniques.

Alternatively where the chosen host is a yeast such as *Saccharomyces cerevisiae* the plasmid YRp7 as the expression vector may be used. One is directed to Stinchcomb et al Nature 282, 39, (1979), Kingsman et al Gene 7; 141 (1979); Tschemper et al, Gene 10; 175 (1980).

On some occasions difficulties were encountered in cloning segments of the *plasmodium falciparum* DNA resulting from the very rich A T DNA sequences which cause problems when cloned in *E coli* organisms.

Using yeasts such as saccharoyces cerevisiae large segments such as 230 kilobases may be cloned successfully using yeast artificial chromosomes such as pYAC-4; Tony Triglia and David Kemp, Molecular and Biochemical Parasitology, 44, 1991, 207-212. As has mentioned herein before the cloning of soluble of T4 peptides has already been achieved and represents little difficulty. One is directed to PCT Patent Application WO 89/11860 and to U.S. Pat. No. 094,322 filed Sep. 4 1987 and to U.S. Pat. No. 141,649 filed January 1987 and the PCT WO 89/01940 filed Sep. 1 1988 which are incorporated here fully by reference.

A wide choice of promoters is available for use in yeast cell expression systems and include by way on non limiting examples 3-phosphoglycerate kinase and one is directed to Hitzman et al J Biol Chem 255; 2073 (1980): also enolase, glyceraldehyde-3-phosphate dehydroginase, hexokinase, pyruvate decarboxylase, phosphofructokinase, glucose-6-phosphate isomerase. 3-phosphoglycerate mutase, pyruvate kinase, triose phosphate isomerase, phospho glucose isomerase ad glucokinaise being glycolytic enzymes and one is directed to Hess et al J Adv Enzyme Reg 7; 149 (1968) and to Holland Biochemistry 17: 4900: 91978.

Other promoters suitable for yeast expression systems include the promoter regions for alcohol deyhydrognase 2, 100 cytocrome C, acid phosphatase, also mettallothioneins, glycoraldehyde-3-phosphate dehydrogenase and others one is directed to Hitzman R et al European patent publication No 73, 657A.

Where insect cells such as Lepidoptera cells are the chosen expression host a suitable vector would be Baculovirus. Such a system would contain the target peptide encoding sequence linked to a baculovirus promoter within a shuttle vector with sufficient baculovirus DNA flanking the target peptide encoding sequence to permit recombination.

One is directed to Summers et al TAES Bull (Texas Agricultural Experimental Station Bulletin) NR 1555 May 1987.

One is also directed to SmithKlein (WO/US/89/05550).

Insect larvae can also be used to produce transformed insect cells, particularly *Heliothis virescens* caterpillars and one is directed to PCT/WO/88/02030 Miller at al.

Where plant cells are the chosen host expression cells the cowpea plant provides a suitable expression system. One is directed to the system developed by the Agriculture Genetics Company of Cambridge UK employing techniques involving the use of cowpea mosaic virus (CPMV).

Where mammalian cells are the chosen hosts for expression, these cells may be grown in vitro in tissue culture or suitable bioreactors or in vivo in animals.

Vectors useful for mammalian cells host systems involve the use of DNA derived from animal viruses such as SV40 virus; retroviruses such as RSV, MMTV, MOMLV, baculovirus. Vaccinovirus, Adenovirus, polyoma or bovine papilloma virus.

Promoters suitable for mammalian cells systems may be chosen from the many available. One is directed to Friers et al Nature 273; 113 (1987) and Greenway P J et al Gene 18; 353-360 (1982) and Okayamah Mol Cell Biol 3; 280; 1; 1983 by way of example.

Additionally suitable enhancers may be chosen from the many available. One is directed to Laimins L et al PNAS 78; 993 (1981) and Lusky M L et al Mol Cell Bio 3; 1108 (1983) and Banerji J L et al Cell 33; 729 (1983) and Osbourne T F et al Mol Cell Bio 4; 1293 (1984).

For a description of some available selection techniques one is directed to Southern et al J Molec Appl Genet 1: 327 (1982) and to Mulligan et al Science 209; 1422 (1980) and to Sugden et al Mol Cell Biol 5; 410-413 (1985).

Some techniques useful for the introduction of the expression vector in to the host cell involve protoplast fusion, calcium phosphate precipitation, electroporation and other techniques as mentioned herein before.

The expression of the fusion peptide or fragment by the host may be confirmed by using an anti CD4 antibody such as a complimentary probe. One is directed to Dalgleish et al Nature 312; 763-766 (1984). Klatzman et al Immunol Today 7; 291-297 1986; McDougal et al J Immunol 153 135; 3151-3162 1985 and McDougal et al J Immunol 137 2937-2944 (1986) and to verification experiments mentioned herein after.

Mammalian host cells suitable for the expression of fragments of, or in some cases the entire fusion peptides may now be chosen from the large number now available such as VERO or CHO-K1, the hybridoma SP2\0-AG14 ot the myloma cell line P3x63Sgh or their P3xSgh derivatives also J558L, cells.

Other suitable eukaryotic host cells include COS cells; human embryonic kidney cells: mouse plasmacytoma cells; mouse sertoli cells; baby hamster kidney cells 98HK cells); Chinese hamster ovary cells—DKFR(CHO); monkey kidney cells; African green monkey cells; human cervical carcinoma cells (HELA cells); human liver cells, and mouse mammary tumour cells by way of non limiting examples.

It will be appreciated that the chosen host cells will preferably express the minimum levels proteases within their cytoplasm. It will also be appreciated that amino acid sequence variations of the peptide sequences involved may be insertions, substitutional or deletional variations involving single amino acid residues or peptide fragments: combinations of or multiples of such variations, or strain or species variation.

The purpose of such variations may be to increase the affinity of the components, to improve stability, to reduce the cost of preparation or to increase the half life, or to lesson the severity of side effects such as atopic reactions. The final form of the molecular machines of the present disclosure may involve any combination of substitutions, delations or insertion of amino acid sequences, provided the binding ability of the epitopes or peptide sequences are retained. It will be appreciated that also included in the present disclosure are glycosylation variations ie variants completely unglycolated, variants having glycosylated amino acids other than those glycosylated in the natural peptides or variants having a greater number of amino acid residues glycosylated or fewer glycosylated residues or residues glycosylated by oligosaccharides other than those oligosaccharides usually associated with the said sequences.

Following their expression by the host cell, the peptides are recovered and purified by means known to the ordinary skilled artisan.

Such methods may include acid extraction, ethanol precipitation using amonium sulphate, anion or cation exchange chromatography, phosphocellulose chromatography, amino affinity chromatography, hydroxyappetite chromatography and reverse phase chromatography.

Generally purification and processing involves four stages:

1) extraction of peptides from host cells;

2) initial purification;

3) final purification:

4) product polishing.

Extraction may be accomplished using sonication techniques; or solid shear techniques—on a small scale.

Lysozyme based techniques are expensive. More usually in the case of bacterial hosts homogenisers or liquid shear techniques are employed.

Other useful techniques involve osmotic shock, freezing and thawing or alkali homogenisation.

In the case where a product is expressed as an inclusion body cell paste may be soublised by solvents such as 8M-guanidinium.

Centrifugation provides the removal cellular debris, and continuous flow centrifuges are preferred for large scale operations. As an alternative to centrafugation cross flow filtration using flat or tubular membranes and high shear forces may provide a useful alternative to centrifugation.

Initial purification involves mainly the removal of excess water and product concentration.

Precipitation using amonium sulphate, organic solvents, polyethylene glycol or other polymers can be used to accomplish this step; with the addition of some variety of chromatography usually absorptive chromatagraphy techniques employing ion exchange, hydrophobic or bioaffinity interactions; followed by washing and desorption; chromatography is not restricted to columns by may take place in membranes or even in spirally wound cartridges.

In cases where peptide fragments have been expressed as inclusion bodies an additional step of 'refolding' is required. Because of low yields after refolding inclusion body production is often uneconomical. However two approaches are practised to refold peptides into the natural or desired three dimensional state; the empirical approach and the rationalist approach.

In the empirical approach multiple solvents are applied and an optimum strategy is determined using phase diagrams as disclosed by Ahmed and Biglow 1979 J Mol Biol 131; 6097-6017

The rationalist approach seeks to produce conditions favouring the native state while at the same time keeping intermediates in solution.

A problem may arise in connection with disulphide bridges which may form in non-native configurations. A way around this problem is to oxidise disulphides under denaturing conditions, using gel filtration remove covalent aggregates and thereafter dilute the product in a non denaturing buffer. The peptide which collapses into an amorphous tangle often rearranges itself into the native form.

Highly resolving chromatography is the preferred technique for final purification. For large scale applications columns are preferred and techniques such as gel filtration, ion exchange, hydrophobic interaction or affinity chromatography may be used alone or in combination as dictated by economies of scale.

Gel filtration is best suited to small batch volumes and suffers from the disadvantage of slow speed.

Ion exchange chromatography techniques are very useful in early purification stages and can deal with large volumes at great speed, producing yields of high resolution.

Hydrophobic interaction chromatography provides both high resolution and high speed even at large batch volumes.

Bio affinity chromatography produces the highest resolution, at high speed, but batch size may require curtailment. This technique is an ideal late stage technique.

The increasing availability of monoclonal antibodies at lower prices has led to greater use of bio affinity chromatographic techniques.

A wide choice of chromatographic matrices is now available on the market suitable for large scale use.

Particle size is decreasing from the 90 um of traditional gels to approximately 40 um for newer gels such as Sepharose HR(R); Sephacryl HR(R); Superdex (R) (Pharmcia—LKB) or Fractogel (R) (Toso-Haas).

Other polymeric particles are Superose (R) (Pharmacia—LKB) or the TSK-PW (R) varieties manufactured by (Toso Haas, Philadelphia USA), providing very low particle size.

It will be appreciated that the process of chromatography involves the choice and development of a strategy containing one or more steps ie high resolution by single step or a multistep procedure the final choice to be determined by:

1) the chosen peptide production process which determines the form of the starting materials to be purified
2) cost Usually the first chromatography column will involve large diameter packings circa 100 um which are often chosen so that they can by resanitised by sodium hydroxide to reduce costs. Low resolution steps to be followed by higher resolution steps until the desired product purity is obtained.

A typical strategy might involve:

Step One Hydrophobic interaction chromatography at low ionic strength. Purpose to absorb proteinases. Target peptides not absorbed and collected. Alternatively use proteinase inhibitors.

Step Two Rerun through hlc column adding salts to bind the target peptide to the hlc column. The objective is volume reduction. Alternatively employ ultra filtration as described. Use a step gradient to elute the target peptide.

Stage Three A step gradient to a low ionic strength buffer will remove remaining salts. Alternatively employ polyethyleneimine precipitation, centrifugation and diafiltration.

In the case of therapeutic peptides such as the molecular machines of this disclosure where administration to a human is considered then the step of product polishing is vital.

Product polishing involves the removal of polymers of the product and other pyrogens.

Techniques for product polishing involve additional gel filtration with or without a buffer exchange step; treatment with alyhdrogel (aluminim hydroxide) or treatment with specific lecithins or anion exchanges.

Following their extraction and purification the hybrid peptides may be combined with carriers, binders, preservatives, antioxidants, antimicrobial agents and the like to formulate a pharmaceutical composition; and one is directed to the British and American Pharmacopoea incorporated herein by reference. It is anticipated that intravenous administration of injectable compositions will be a principle route of administration of the hybrid peptides. However other compositions for administration include microphores, lyosomes or sustained release formulations, replantable or microcapsular sustained release matrices; intra muscular administration may also be used.

The hybrid peptides may also be components of capsules, tablets, creams, gels, lotions, drops, patches or may be administered where appropriate by any other of the known means of administration of a drug to a human where appropriate.

Hydro phobic solvents may be used for intravenous or parental administration in some circumstances. Examples of such solvents are propylene glycol, polyethylene glycol, vegetable oils, organic esters.

Aqueous carriers which are preferred are by way of example water for injection, emulsions or suspensions, saline or buffers, alcoholic aqueous solutions, sodium chloride solutions, ringers lactate or dextrose.

The manufacturing process only finishes with the secure packaging of the peptides in a suitable vacuum or atmosphere in suitable containers usually vials of glass or polymers with suitable stoppers. The said glass or polymer vials are then housed in a sturdy housing of cardboard or polymer after appropriate sealing. The cardboard housing will ideally be further wrapped in a clear polymer such as cellulose and provided with a seal to disclose tampering. All relevant information such as product name, date of manufacture, batch number and date of expiry and the like should be clearly visible and printed on the vials and housing as required by law and good manufacturing practice. The products should also be accompanied by leaflets, indicating material facts relevant to their use such as dosage, side effects, contra indications and the like it will be appreciated that the manufacturing process should take place in an appropriately designed facility, the-floors, walls and ceilings of which should be finished to a high standard. Product flow must be arranged to reduce risk of mix up. Water systems employed should meet the US Pharmacopia specifications for pure water and be of injection quality in final purification stages.

Compressed air and nitrogen must be filtered through 0.2 u inch filters and be free of oil.

Final purification stages should ideally take place under laminate flow hoods or equivalent in suitably clean rooms.

In short the manufacture of the peptides must take place in conditions meeting GMP standards.

Validation and quality control are ongoing necessary steps to ensure public safety and product quality.

The disclosure will be illustrated by means of exemplary embodiments which are non limiting.

In the exemplary embodiments that follow a number of assumptions are made which will be appreciated by the reader, these assumptions to being common knowledge to persons skilled in the art.

within the scope and spirit of the invention if used for the same purpose and in the 'same way' as the molecular machines of the invention.

Exemplary Embodiment Number 1

Exemplary embodiment number 1 is directed to a molecular machine or hybrid protein which comprises a peptide sequence derived from the CD4 molecule or fragment thereof which possesses the capability of binding to HIV GP120, fused to a peptide sequence or fragment thereof derived from the merozoite glycophorin binding peptide GBP130.

The peptide sequence of the CD4 molecule providing derived fragments useful for the preparation for the first component was disclosed by Paul Jay Maddon et al in Cell, Vol 42, 93-104, August 1985. See FIG. 6 page 97; incorporated fully herein by reference.

The second component peptide of the hybrid peptide of the present embodiment may be derived from the peptide sequence of GBP130 glycophorin binding peptide 130 as disclosed by Jarema Kochan et al in Cell Vol 44, 689-696 March 14 1986. See FIG. 2 page 691 and incorporated fully herein by reference.

In this example the peptide sequence consisting of 1-371 of the CD4 molecule is fused at the C terminal end to the N terminal end of a peptide sequence derived from the GBP130 molecule amino acid residues 201-774 of the GBP molecule or a fragment thereof.

```
      +1                                       371
      Gln.............................. Val...................................... Ala
                                         201                                      774

NH2---------- CD4----------------- |-----------------GBP130-----------------COOH
                                         CN
```

1) It is generally considered easier by all arts from DNA cloning to woodworking to delete ie shorten an object than to add to it. Therefore peptide sequences as useful formulae longer than necessary will be provided by way of illustration; truncation or deletions to be carried out as desired.

2) Any substitutions and any modifications of the wild type CD4 or indeed the malaria erythrocyte binding molecules will fall within the scope and the spirit of the invention. Avi Ashkanazi et al Proceedings national Academy of Science USA Vol 87, p 7150-7154 Sep. 1990 reports substitution experiments where alanine residues were substituted for naturally occurring amino acid residues within the CD4 molecule. The results demonstrated that single alanine substitution made little difference in most cases to the ability of CD4 segments to bind to the HIV GP120. In some cases either no binding whatsoever was found or greatly improved binding was found more particularly the substitutions G4OA and D63A; of special interest are the double substitution G4OA and D63A which exhibited a 2.3 fold increase in affinity and the triple mutant Q40A D63A Q89L which exhibited a four fold affinity increase.

3) It is common knowledge that species variation or strain variations of peptides exist in nature. Accordingly it will be appreciated the peptide segments derived from proteins of any strain of the malaria organism, filling the same role fall In this example the preferred fusion is by peptide bonds, it will also be appreciated that the site of fusion is illustrative but not limiting. Fusion may take place at other amino acid residues of both the above peptide components. The example will be further described by a useful formula of

```
            NH2-CD4------------GBP130-COOH
              1-371              207-774
``` to avoid any possible confusion Therefore the formula of

```
            NH2-CD4-GBP130 COOH
              1-371   201-774
``` in would aspect would be, SEQ. ID. No. 1:

```
            +1                            10                            20
N Terminal  gln gly asn lys val val leu gly lys lys gly asp thr val glu leu thr cys thr ala ser gln lys lys ser ile gln phe his trp lys asn ser asn gln ile lys ile leu gly asn gln gly ser phe leu thr lys gly pro ser lys leu asn asp arg ala asp ser arg arg ser leu trp asp gln gly asn phe pro leu ile ile lys asn leu lys ile glu asp ser asp thr tyr ile cys glu val glu asp gln lys glu glu val gln leu leu val phe gly leu thr ala asn ser asp thr his leu leu gln gly gln ser leu thr leu thr leu glu ser pro pro gly ser ser pro ser val gln cys arg ser pro arg gly lys asn ile gln gly gly lys thr leu ser val ser gln leu glu leu gln asp ser gly thr trp thr cys thr val leu gln asn gln lys lys val glu phe lys ile asp ile val val leu ala phe gln lys ala ser ser ile val tyr lys lys glu gly glu gln val glu phe ser phe pro leu ala phe thr val glu lys leu thr gly ser gly glu leu trp trp gln ala glu arg ala ser ser ser lys ser trp ile thr phe asp leu lys asn lys glu val ser val lys arg val thr gln asp pro lys leu gln met gly lys lys leu pro leu his leu thr leu pro gln ala leu pro gln tyr ala gly ser gly asn leu thr leu ala leu glu ala lys thr gly lys leu his gln glu val asn leu val val met arg ala thr gln leu gln lys asn leu thr cys glu val trp gly pro thr ser pro lys leu met leu ser leu lys leu glu asn lys glu ala lys val ser lys arg glu lys ala val trp val leu asn pro glu ala gly met trp gln cys leu leu ser asp ser gly gln val leu leu glu ser asn ile lys val leu pro thr trp ser thr pro val ser gln lys pro ser thr ser thr arg ser asn asn glu val lys ile arg ala ala ser asn gln glu thr leu thr ser ala asp pro glu gly gln ile met arg glu tyr ala ala asp pro glu tyr arg lys his leu glu ile phe tyr lys ile leu thr asn thr asp pro asn asp glu val glu arg arg asn ala asp asn lys glu asp leu thr ser ala asp pro glu gly gln ile met arg glu tyr ala ser asp pro glu tyr arg lys his leu glu ile phe tyr lys ile leu thr asn thr asp pro asn asp asp val glu arg arg asn ala asp asn lys glu asp leu thr ser ala asp pro glu gly gln ile met arg glu tyr ala ala asp pro glu tyr arg lys his leu glu val phe his lys ile leu thr asn thr asp pro asn asp glu val glu arg arg asn ala asp asn lys glu asp leu thr ser ala asp pro glu gly gln ile met arg glu tyr ala ala asp pro glu tyr arg lys his leu glu ile phe his lys ile leu thr asn thr asp pro asn asp glu val glu arg arg asn ala asp asn lys glu asp leu thr ser ala asp pro glu gly gln ile met arg glu tyr ala ala asp pro glu tyr arg lys his leu glu val phe his lys ile leu thr asn thr asp pro asn asp glu val glu arg arg asn ala asp asn lys glu leu thr ser ser asp pro glu gly gln ile met arg glu tyr ala ala asp pro glu tyr arg lys his leu glu ile phe his lys ile leu thr asn thr asp pro asn asp glu val glu arg arg asn ala asp asn lys glu asp leu thr ser ala asp pro glu gly gln ile met arg glu tyr ala ala asp pro glu tyr arg lys his leu glu ile phe tyr lys ile leu thr asn thr asp pro asn asp glu val glu arg arg asn ala asp asn lys glu asp leu thr ser ala asp pro glu gly gln ile met arg glu tyr ala ala asp pro glu his leu glu ile phe his lys ile leu thr asn thr asp pro asn asp glu val glu arg arg asn ala asp asn lys glu glu leu thr ser ser asp pro glu gly gln ile met arg glu tyr ala ala asp pro glu tyr arg lys his leu glu ile phe tyr lys ile leu thr asn thr asp pro asn asp glu val glu arg arg asn ala asp asn lys glu asp leu thr ser ala asp pro glu gly gln ile met arg glu tyr ala ser asp pro glu tyr arg lys his leu glu ile phe tyr lys ile leu thr asn thr asp pro asn asp asp val glu arg arg asn ala asp asn lys glu asp
```

-continued leu thr ser ala asp pro gly glu gln ile met arg glu tyr ala ala asp pro glu tyr arg lys his leu glu ile phe his lys ile leu thr asn thr asp pro pro asn asp glu val glu arg gl:n asn ala asp asn asn glu ala - C TERMINAL, which formula describes the embodiment but is intended to be non limiting.

This exemplary embodiment is also directed to a protein gene which comprises a DNA sequence which codes for the CD4 molecule or fragment thereof which binds HIV GP120 fused to a DNA sequence which encodes the glyphorin 130 or fragment thereof which possesses the capability of binding to red cells.

DNA sequences suitable for forming the cloned DNA of the fusion peptide may be found in the disclosure of Paul Jay Maddon Cell, Vol 42 93-104. August 1985 see FIG. 6 page 97. Some or all of the DNA sequence coding for the CD4 molecule as disclosed may be fused to the DNA sequence conditioning for the DNA glyphorin binding peptide. It may be preferable to include the leader sequence of the CD4 molecule. It may also be preferable to delete the transmembrane and cytoplasmic domains. A DNA sequence encoding the glycophorin peptide 130 and suitable for the fabrication for the cloned genes useful for the preparation of the hybrid peptides of this disclosure may be found in Jarema Kochan et al Cell Vol 4 689-696 Mar. 14, 1986 FIG. 2 page 691. Suitable sites of fusion might be in the region of site 733 ie Leu AAA or in the vicinity of site 736 ie val, GTT or in the vicinity of Site 739 ie Ser TCT in the case of GBP130; and in the region of site 1257 for the CD4 derived sequence.

```
-17                 +371  +202               +774
met................ val   ser................ ala 76                  1257  737                2455
ATG................ GTG   TCT.................GCA
        CD4                      GBP130
```

By way of further illustration the CD4 DNA sequence is restricted at the BspM1 site position 514 and fused to some or all of the DNA sequence coding for GBP130 as disclosed above or restricted at other convenient sites

```
|--------  CD4-----------|------------GBP130-----|
                       BSPM1
                        514
```

The DNA sequence for the CD4 component is also obtained by restricting the DNA sequence encoding for the CD4 peptide component as previously disclosed at the Pvu11 site, position 691 and joined to the cloned DNA encoding the glycophorin binding peptide 130 fragment as previously described or smaller fragments thereof, restricted as desired.

```
|--------  CD4-----------|------------GBP130-----|
                       Pvu11
                        629
```

Fusion will be carried out by suitable ligases and gene fragments, even those gene fragments encoding additional amino acids or sequences of amino acids may be inserted to enable the ligation provided the inserted segments do not, interfere with the functionality of either the CD4 derived peptide or the GBP130 derived peptide segment.

It is also envisaged that the hybrid peptide will have 2 components: the first being a CD4 derived peptide sequence comprising amino acids 1-177 ie +1 gln-177 val fused to a glyophorin binding protein (GBP) 130 derived peptide sequence such as Leu 226-Ala 774 or Thr 227 Ala 274, fusion to take place at Leu 226 or Thr 227 by way of example fusion to consist of a peptide bond formed between CD4 amino acid 177 and the glycophrin binding peptide 130 amino acid 226 or 227 fused at the C terminal end of the CD4 derived peptide and the N terminal end of the GBP130 peptide sequence. The said sequences and the enumeration of the said sequences to be found in the sources mentioned herein before.

This variation of the embodiment contains only the tandem repeat sequence of the GBP-130 molecule.

```
Gln                Val Thr                   Ala
+1                 177 227                   774
|-------   CD4---------|--------GBP130----------|
                                                C
```

In this exemplary embodiment it is also envisaged that a peptide sequence comprising the first 117 amino acids of the CD4 molecule or fragment thereof are fused C terminally to a peptide sequence of the glycophorin binding peptide GBP130. A suitable site of fusion would be Ala 370 N terminally to provide an amino acid lead sequence to be followed by the tandem repeat sequence beginning with Leu 376; the sequence terminating at Asp 425. It is appreciated that smaller sections of such a tandem sequence could be used as can smaller sections of the CD4 peptide sequence. The example is intended to be illustrative rather than limiting.

```
1                              177 370..376                         425
Gln--------------------        Val-Ala----Leu----------------------  Asp

N----------------  CD4----------|-----------              GBP-130-----  C
                                             single tandem repeat
```

In all the preceeding variations of exemplary embodiment number 1 the CD4 component peptide may be fused at the N terminal end to the C terminal end of the GBP130 derived peptide sequence. It was shown by P Yeh et al PNAS March 1992 P1904-1908 that functionality is not lost when CD4 is fused N terminally.

Exemplary Embodiment Number 2

This exemplary embodiment is directed to a molecular machine or hybrid peptide characterised by the fusion of some or all of the amino acid peptide sequence, amino acid residues 1-371 of the CD4 molecule fused at the C terminal end to a peptide sequence derived from the glycophorin binding peptide homologue molecule. Amino acid resides 70-427 or segments thereof of the glyophorin binding peptide homolgue(s). The amino acid sequence of the CD4 molecule has been disclosed by Paul Jay Maddon, the reference is given in Exemplary Embodiment No. 1. The glycophorin binding peptide homologue amino acid sequence is disclosed by Dagmar Nolte et al in Molecular and Biochem Parasitology 49, (1991) page 253-264 FIG. 2 page 257, incorporated fully herein by reference.

```
         gln            val-ser                ser
      N|------CD4-------|------GBPH------------|C
      +1              371 70                  427
```

It may avoid confusion to describe the exemplary embodiment in one aspect by a useful formula which is intended to be non limiting.

Therefore the formula of

```
            NH2   CD4-GBPH-COOH
                  1-371 70-427
``` in one aspect is; SEQ. ID. No. 2:

N Terminal QGNKVVLGKKGDTVELTCTASQKKSIQFHWKNSN

QIKILGNQGSFLTKGPSKLNDRADSRRSLWDQGNFPLIIKNL

KIEDSDTYICEVEDQKEEVQLLVFGLTANSDTHLLQGQSLT

LTLESPPGSSPSVQCRSPRGKNIQGGKTLSVSQLELQDSGT

WTCTVLQNQKKVEFKIDIVVLAFQKASSIVYKKEGEQVEFS

FPLAFTVEKLTGSGELWWQAERASSSKSWITFDLKNKEVS

VKRVTQDPKLQMGKKLPLHLTLPQALPQYAGSGNLTLALEA

KTGKLHQEVNLVVMRATQLQKNLTCEVWGPTSPKLMLSLK

LENKEAKVSKREKAVWVLNPEAGMWQCLLSDSGQVLLESN

IKVLPTWSTPVSQYKQAADYSFRESRVLAEGKSTSKKNAK

TALRKTKQTTLTSADPEGQIMKAWAADPEYRKHLNVLYQI

LNNTDPNDELETSADPEGQIMKAYAADPEYRKHLNVLYQIL

NNTDPNDEVESSADPEGQIMKAYAADPEYRKHVNVLYQIL

NNTDPNDELETSADPEGQIMKAYAADPEYRKHVNVLYQILN

HTDSSEVETSADPEGQIMKAYAADPEYRKHVNVLYQILNH

TDSSEVETSADPEGQIMKAYAADPEYRKHVNVLYQILNNTD

PNDELETSADPEGQIMKAYAADPEYRKHVNVLYQILNNTDP

NDELETSADPEGQIMKAYAADPEYRKHVNVLYQILNNTDPN

DESS-C Terminal;

which formula is but one possible variation of the many apparent to the skilled artisan.

This example is also directed to a molecular machine or fusion peptide which is characterised by the fusion of CD4 peptide sequence to a glycophorin binding peptide homologue sequence. The CD4 derived sequence comprises some or all of the amino acids from number 1-177 of the CD4 molecule. The sequence numbering and source of CD4 peptide sequence has been referenced herein before, see exemplary embodiment No. 1.

The above CD4 peptide sequence to be fused C terminally to the N terminal of glycophorin binding homologue peptide sequence amino acid residues 70-427 or some or part thereof. The source of glycophorin binding peptide homologue being the sequence disclosed by Dagmar Nolte (full reference given above).

```
         gln                  val - ser                               ser
      N|---------CD4----------------|-------------------------GBPH--------------|C
      +1                           177 70                                      427
```

This example is also directed to a molecular machine or hybrid peptide formed by the fusion of an amino acid peptide sequence derived from the CD4 molecule amino acid residues 1-371 or fragment thereof fused C terminally to a peptide sequence derived from the glycophorin binding peptide homologue fused N terminally at amino acid 109; the sequence comprising amino acids 109-427 some or part thereof. The sequencing of CD4 and glycophorin peptide binding homologue as already referenced.

```
         gln-------------- val-leu-------------------- ser
      N|....CD4...........----|----........GBPH........|C
      +1                     371 109                  427
```

This example is also directed to a molecular machine or hybrid peptide which comprises the fusion of an amino sequence derived from the CD4 molecule the sequence as previously disclosed and consists of amino acid residues 1-177 or fragments thereof fused C terminally to a tandem repeat sequence(s) derived from the glycophorin peptide binding homologue molecule as disclosed herein before. Such a sequence may consist of amino acid residues 230-268. It will be appreciated that an even shorter fragment could be used. It will be also appreciated that one or more of the tandem repeat sequences could be included. It will be further appreciated that the tandem repeat sequence could be shortened to an even smaller fragment containing only the RBC binding epitopes: and that this smaller fragment could be repeated.

It will be still further appreciated that related glycophorin binding peptide homologue molecules whose sequences are known but not as yet disclosed in the public domain could provide peptide sequences—tandem repeat units—fulfilling the functions of GBP130 or the GBPH sequences as disclosed above "in the same way" without departing from the scope and spirit of the invention.

```
         gln------------------  val-thr----------------   glu
      N|-----------CD4----------|---------GBPH-------|C
      1                        177 230 single tandem 268
                                        repeat
```

This example is further directed to a fused gene coding for a hybrid peptide comprising a amino acid sequence derived from the CD4 molecule joined to an amino acid sequence derived from the glycophorin binding peptide homologue molecule. A typical fused gene might consist of;

```
ATG..     CAG........CCC..............ACT.........GAA
76        144        514              1369        1488
|-------|-CD4--------------|--X----------|-----GBPH--------|
         Bspm1                                single tandem
                                              repeat
```

Where X is any or no intervening sequence, X being inspecified any non limiting.

Ligation to take place using ligases and additional linker segments by conventional means, known to the skilled artisan.

This example is further directed to a fusion gene consisting of a DNA sequence encoding a peptide derived from the CD4 molecule truncated at the PvuII site 691 fused to a single tandem repeat encoding DNA sequence derived from glycophorin binding peptide homologue gene as disclosed by Nolte as referenced herein before or part thereof.

```
ATG....CAG............ACC.........ATC..........GAA
76     144            629         1369          1488
|--------|----- CD4--------|-----X--------|----GBPH---------|
                Pvu11                           single tandem
                                                repeat
```

Where X is any intervening sequence X being inspecified and non limiting. Suitable linkers and joining segments to be provided as desired.

All the preceding exemplary embodiments may be fused C terminally of CD4 segment to the N terminal of the GBPH component.

Exemplary Embodiment Number 3

This example is directed to a molecular machine or hybrid peptide formed by the fusion of a peptide sequence derived from the CD4 molecule or fragment thereof; the amino acid resides 1-371 fused at their C terminal end to a peptide sequence derived from the EBA 175 antigen otherwise known as the erythrocyte binding antigen 175; amino acid residues 20-1435 all or part thereof. In this example some or all ie fragments of the component peptide sequences may be used to fabricate the hybrid peptide. The sequence of amino acids and DNA sequence of the gene encoding EBA 175 was disclosed by B Kim Lee Sim et al in the Journal Cell Biology Vol 111, 1990 p 1877-1884, FIG. 2, p 1880; incorporated fully herein by reference. The peptide sequence for CD4 being already referenced herein before.

```
|——————CD4————————---|—————EBA-175——————|
N                                       C
1                    371 20             1435
```

To avoid any possible confusion it may be helpful to describe the embodiment by a useful formula which is intended as non limiting.

CD4 is truncated at 371 and EBA-175 truncated at 19 ie excluding the hydrophobic sequence. CD4 after Maddon. EBA-175 after Klm Lee Sim J Cell Biology Vol 111 1990, 1880

Therefore the molecular machines $NH_2$ CD4-EBA 175-COOH
1-371 20-1435 in one aspect would be: SEQ. ID. No. 3:

N Terminal QGNKVVLGKKGDTVELTCTASQKKSIQFHWKNSN

QIKILGNQGSFLTKGPSKLNDRADSRRSLWDQGNFPLIIKNL

KIEDSDTYICEVEDQKEEVQLLVFGLTANSDTHLLQGQSLT

LTLESPPGSSPSVQCRSPRGKNIQGGKTLSVSQLELQDSGT

WTCTVLQNQKKVEFKIDIVVLAFQKASSIVYKKEGEQVEFS

-continued

FPLAFTVEKLTGSGELWWQAERASSSKSWITFDLKNKEVS

VKRVTQDPKLQMGKKLPLHLTLPQALPQYAGSGNLTLALEA

KTGKLHQEVNLVVMRATQLQKNLTCEVWGPTSPKLMLSLK

LENKEAKVSKREKAVWVLNPEAGMWQCLLSDSGQVLLESN

IKVLPTWSTPVKARNEYDIKENEKFLDVYKEKFNELDKKKY

GNVQKTDKKIFTFIENKLDILNNSKFNKRWKSYGTPDNIDKN

MSLINKHNNEEMFNNNYQSFLSTSSLIKQNKYVPINAVRVS

RILSFLDSRINNGRNTSSNNEVLSNCREKRKGMKWDCKKKN

DRSNYVCIPDRRIQLCIVNLSIIKTYTKETMKDHFIEASKKES

QLLLKKNDNKYNSKFCNDLKNSFLDYGHLAMGNDMDFGGY

STKAENKIQEVFKGAHGEISEHKIKNFRKEWWNEFREKLWE

AMLSEHKNNINNCKNIPQEELQITQWIKEWHGEFLLERDNR

SKLPKSKCKNNTLYEACEKECIDPCMKYRDWIIRSKFEWHT

LSKEYETQKVPKENAENYLIKISENKNDAKVSLLLNNCDAE

YSKYCDCKHTTTLVKSVLNGNDNTIKEKREHIDLDDFSKFG

CDKNSVDTNTKVWECKNPYILSTKDVCVPPRRQELCLGNID

RIYDKNLLMIKEHILAIAIYESRILKRKYKNKDDKEVCKIINK

TFADIRDIIGGTDYWNDLSNRKLVGKINTNSKYVHRNKKND

KLFRDEWWKVIKKDVWNVISWVFKDKTVCKEDDIENIPQFF

RWFSEWGDDYCQDKTKMIETLKVECKEKPCEDDNCKSKCN

SYKEWISKKKEEYNKQAKQYQEYQKGNNYKMYSEFKSIKP

EVYLKKYSEKCSNLNFEDEFKEELHSDYKNKCTMCPEVKDV

PISIIRNNEQTSQEAVPEENTEIAHRTETPSISEGPKGNEQKE

-continued

```
RDDDSLSKISVSPENSRPETDAKDTSNLLKLKGDVDISMPK

AVIGSSPNDNINVTEQGDNISGVNSKPLSDDVRPDKKELED

QNSDESEETVVNHISKSPSINNGDDSGSGSATVSESSSNTG

LSIDDDRNGDTFVRTQDTANTEDVIRKENADKDEDEKGADE

ERHSTSESLSSPEEKMLTDNEGGNSLNHEEVKEHTSNSDNV

QQSGGIVNMNVEKELKDTLENPSSSLDEGKAHEELSEPNLS

SDQDMSNTPGPLDNTSEETTERISNNEYKVNEREDERTLTK

EYEDIVLKSHMNRESDDGELYDENSDLSTVNDESEDAEAKM

KGNDTSEMSHNSSQHIESDQQKNDMKTVGDLGTTHVQNE

ISVPVTGEIDEKLRESKESKIHKAEEERLSHTDIHKINPEDRN

SNTLHLKDIRNEENERHLTNQNINISQERDLQKHGFHTMNN

LHGDGVSERSQINHSHHGNRQDRGGNSGNVLNMRSNNNN

FNNIPSRYNLYDKKLDLDLYENRNDSTTKELIKKLAEINKCE

NEISVKYCDHMIHEEIPLKTCTKEKTRNLCCAVSDYCMSYF

TYDSEEYYNCTKREFDDPSYTCFRKEAFSSMIFKFLITNKIY

YYFYTYKTAKVTIKKINFSLIFFFFFSF - C Terminal,
``` which is intended to be non limiting, variations of which will be apparent to the skilled artisan.

This example is also directed to a molecular machine or fusion peptide comprising the fusion of a peptide sequence derived from CD4 consisting of the first 177 amino acid residues or fragment peptide sequence thereof: amino acid 1-177 fused at the C terminal end to the N terminal end of a peptide sequence derived from EBA 175 amino acid 1062-1103. This particular peptide sequence is also named EBA peptide 4 and has the ability to inhibit the binding of EBA 175 to red blood cells. Also included would be fused genes formed by the fusion of DNA sequences encoding the CD4 molecule fused to Sequences encoding the erythrocyte binding antigen 175 or its derived peptide EBA peptide 4. The DNA sequences of the EBA peptide number 4 and EBA 175 molecules may be obtained from the Journal of Cell Biology Vol 111 1990, p 1880 in the article by J Kim Lee Sim et al in the same journal.

```
N|-----CD4--------|----EBA peptide 4--------|C
1             177   1062                    1103
```

It is also envisaged that the CD4 component may be fused at the N terminal end to the C terminal end of any of the preceding examples.

Exemplary Embodiments Using *P. vivax* Duffy

Exemplary Embodiment Number 4

In this embodiment the P Vivax Duffy Receptor molecule is joined to the CD4 receptor molecule both truncated at their transmembrane extrecellular domain regions.

```
|-P Vivax Duffy----|--|    |--|---CD4 J1-4 V1-4--|
                  Tm  Tm
               deleted Tm region
```

-continued

New molecule

```
H2N- P Vivax Duffy- C      C---- CD4 J1-4 V1-4---NH2
       23 -> 1051                  371 <- 1
                     |___ J ___|
```

J segment or cross linker

Obviously further deletions and substitutions may be made to this molecule without departing from its intended function, the listing of all possible deletions and substitutions obvious to an artisan skilled in the art would be tedious and is excluded in the interests of brevity.

It is to be noted that the amino acid sequence of CD4 as presented in this embodiment is the same as for Maddon P N A Sci 1987 but in reverse order.

It is also to be noted that the CD4 peptide segment may be fused at the N terminal end to the C terminal of the P Vivax Duffy peptide, or at the C terminal end of the CD4 molecule to the N terminal of the P Vivax Duffy Receptor; by peptide bonds. This embodiment is also directed to a molecular machine or hybrid peptide comprising the fusion or joining together of two amino acid sequences: one derived from the CD4 molecule and consisting some of a fragment of amino acid or peptide sequence derived from *plasmodium Vivax* Duffy Receptor molecule or fragment thereof; amino acid sequence 23-1051 joined at the C terminal ends which will require that the component sequences be expressed separately in separate hosts and fused subsequently. Many strategies are available for joining two peptide sequences together at both C terminal ends. One strategy envisages terminating both peptide sequences with 'cys' or incorporating cys near each C terminal end and fusion of the two sequences by means of sulphidryl bonds. Other strategies involve the use of joining sequences containing cys facilitating sulphidryl bonds linking the joining segment to the component peptide sequences. The genetic sequence and amino acid sequence of *Plasmodium Vivax* Duffy Receptor is disclosed by Xiangdang Fang et al in Molecular and Biochemical Parasitology 44. (1991) 125-132 one is directed to FIG. 1 of p 127.

```
                          Chemical
                          linker
                          agent
       P Vivax Duffy     /       \              CD4
    N|-----------------|C        C|----------------|N
                      1051       371               1
       P Vivax Duffy                              CD4
    N|---------------------cys-s-s-cys-------------|N
       23 receptor  1051         371               1
                    insert       insert
       P Vivax Duffy                              CD4
    N|-----------cys----|C        C|----cys--------|N
       23 receptor    s 1051    371    s           1
                      |                |
                      s                s
                      |                |
                      |----cys--------J------cys--|
```

It may be helpful to describe the molecular machines by a useful formula of a amino acids, the useful formula is intended to be non limiting.

Therefore a useful formula

```
for  N——P Vivax Duffy——C     C——CD4 J1-4 VI-4——N
 8        23 -> 1051    :     :       371 <- 1
                        ‾——J——‾
```

Where J is a joining segment or cross linker in one aspect would be: SEQ. ID. No. 4: and SEQ. ID. No. 5:

KDDFSITLINYHEGKKYLIILKRKLEKANNRDVCNFFLHFSQ

VNNVLLERTIETLLECKNEYVKGENGYKLAKGHHCVEEDNL

ERWLQGTNERRSEENIKYKYGVTELKIKYAQMNGKRSSRIL

KESIYGAHNFGGNSYMEGKDGGDKTGEEKDGEHKTDSKTD

NGKGANNLVMLDYETSSNGQPAGTLDNVLEFVTGHEGNSR

KNSSNGGNPYDIDHKKTISSAIINHAFLQNTVMKNCNYKRK

RRERDWDCNTKKDVCIPDRRYQLCMKELTNLVNNTDTNFH

RDITFRKLYLKRKLIYDAAVEGDLLLKLNNYRYNKDFCKDIR

WSLGDFGDIIMGTDMEGIGYSKVVENNLRSIFGTDEKAQQR

RKQWWNESKAQIWTAMMYSVKKRLKGNFIWICKLNVAVN

IEPQIYRWIREWGRDYVSELPTEVQKLKEKCDGKINYTDKK

VCKVPPCQNACKSYDQWITRKKNQWDVLSNKFISVKNAEK

VQTAGIVTPYDILKQELDEFNEVAFENEINKRDGAYIELCVC

SVEEAKKNTQEVVTNVDNAAKSQATNSNPISQPVDSSKAE

KVPGDSTHGNVNSGQDSSTTGKAVTGDGQNGNQTPAESD

VQRSDIAESVSAKNVDPQKSVSKRSDDTASVTGIAEAGKE

NLGASNSRPSESTVEANSPGDDTVNSASIPVVSGENPLVTP

YNGLRHSKDNSDSDGPAESMANPDSNSKGETGKGQDNDM

AKATKDSSNSSDGTSSATGDTTDAVDREINKGVPEDRDKT

VGSKDGGGEDNSANKDAATVVGEDRIRENSAGGSTNDRSK

NDTEKNGASTPDSKQSEDATALSKTESLESTESGDRTTNDT

TNSLENKNGGKEKDLQKHDFKSNDTPNEEPNSDQTTDAEG

HDRDSIKNDKAERRKHMNKDTFTKNTNSHHLNSNNNLSNG

KLDIKEYKYRDVKATREDIILMSSVRKCNNNISLEYCNSVED

KISSNTCSREKSKNLCCSISDFCLNYFDVYSYEYLSCMKKE

FEDPSYKCFTKGGFK

```
       -COOH CROSSLINKER  COOH VPTSETP
        terminal
                OR
                JOINING
                SEQUENCE
  insert cys in Duffy    insert cys in CD4
  and insert cys in          and insert cys in
  J sequence       J      J sequence
```

LVKINSELLVQGSDSLLCQWMGAEPNLVWVAKERKSVKAE

KNELKLSLMLKPSTPGWVECTLNKQLQTARMVVLNVEQHL

KGTKAELALTNNGSGAYQPLAQPLTLHLPLKKGMQLKPDQ

TVRKVSVEKNKLDFTIWSKSSSAREAQWWLEGSGTLKEVT

FALPFSFEVQEGEKKYVISSAKQFALVVIDIKFEVKKQNQLV

TCTWTGSDQLELQSVSLTKGGQINKGRPSRCQVSPSSGPP

SELTLTLSQGQLLHTDSNATLGFVLLQVEEKQDEVECIYTD

SDEIKLNKIILPFNGQDWLSRRSDARDNLKSPGKTLFSGQN

GLIKIQNSNKWHFQISKKQSATCLEVTDGKKGLVVKNGQ

NH$_2$ Terminal;

the numbering of this useful formula is after that of the referenced sourced peptides. It will be appreciated that the skilled artisan could provide countless variations on the above without departing from the scope and spirit of the disclosure.

Exemplary Embodiment Number 5

This example is directed to a molecular machine or hybrid peptide formed by the fusion of a peptide sequence derived from the P Knowlesi Duffy Receptor binding molecule as disclosed by Xiangdong Fang in Molecular and Biochemical Parasitology 44, (1991) 125-132 see FIG. 1 P 127. The choice of peptide fragment is non critical provided it contains erythrocyte binding ability and the method of joining to the CD4 component is also non critical, examples of typical methods of joining peptides are given in the preceding examples.

```
       P Knowlesi
       Duffy receptor                              CD4 receptor
    N|——————————————cys—C     C—cys——————————————|N
                      |             |
                      s             s
                      |             |
                      s             s
                      |             |
                    |—cys————J————cys—|
```

The fusion may also be by peptide bonds N terminal of CD4 component to C terminal of P Knowlesi or N terminal of P Knowlesi component to C terminal of CD4 component Exemplary Embodiment Number 6

This example is directed to a molecular machine or hybrid peptide formed by the fusion of a peptide sequence derived from the expression of the PMMSA gene or precursor to the major merozoite surface antigen genes as disclosed by M Gregory Peterson in Molecular and Biochemical Parasitology, 27 (1988) P 291-302. One is directed to p294, and p295 FIG. 3.

In this example an amino acid sequence derived from the expression of nucleic acid residues 177-5169 all or part fused at the C terminal end to the C terminal end of the CD4 derived peptide sequence such as formed from the expression of nucleic acid residues 114-1260 or fragment thereof.

The fusion at the C terminal end being accomplished by suitable joining sequences chemical ligands or sulphidryl bonds, or other means.

It will also be envisaged that cys residues be added as required as described in exemplary embodiment number 14; the site of insertion is non critical providing binding function is maintained.

```
           PMMSA                        CD4
    177├──── Nuc acid ────┤5169   1260├──── Nuc acid ────┤114
                    ↑                          ↑
                  insert                     insert
                   cys                        cys
                    └──────── J segment ────────┘
                                fusion
```

Alternatively a fused gene joining the CD4 component to the PMMSA component N terminally to C terminally by peptide bonds may be utilised to provide alternative variations apparent to the skilled artisan.

Exemplary Embodiment Number 7

Exemplary embodiment number 7 contemplates joining sequences suitable for joining two peptide fragments at the C terminal ends. The joining sequences could be a straight peptide chain which will have cys amino acid residues added to form sulphidryl bonds with cys residues also inserted into the peptide sequences to be joined. Other methods of ligation are also envisaged. A suitable straight segment, but by no means the only suitable straight segment may be found in the joining chain amino acid residues 95-112 inclusive of the CD4 molecule; the sequence disclosed by Paul Jay Maddon and already referenced herein before. 'Cys' residues may be inserted at any site for example between amino acid 97 and 98 and between 107 and 108 to name but two possible sites.

The CD4 molecule is part of the immunoglobulin superfamily.

The immunoglobulin superfamily provide many examples of straight and bent chains with cys already inserted for the purposes of such bonding.

One is free to choose from any of these peptide segments without departing from the scope and spirit of the invention as disclosed.

One is also free to use other straight or bent peptide sequences. SEQ. ID. No. 6:

```
N H₂ val.gln.leu.leu.val.phe.gly.leu.thr.ala.asn.asn.ser.asp.thr.his.leu.leu.gln. C Term
           insert                        insert
            cys                           cys
```

Exemplary Embodiment Number 8

Exemplary embodiment number 8 illustrates how a joining sequence J can be used to join an EBA175 fragment with a GBP130 fragment and both to be joined to a CD4 derived peptide or variations already listed. The J peptide sequence may be similar to that already provided or have additional cys residues added.

```
        GBP130                                    EBA-175
    774├──── cys ────┤202          20├──── cys ────────┤1435
              │                              │
              s                              s
              │                              │
              s                              s
              │                              │
    ├--J segment── cys ──────── cys ──────── cys ──┤
                              │
                              s
                              │
                              s
                              │
                     ├──────── cys ────────┤
                        371    CD4        1
```

It will be appreciated that branched chains such as the one illustrated or variations thereof, anyone of which functioning in the same way would be apparent to the skilled artisan and fall within the scope and spirit of the disclosure.

Exemplary Embodiment Number 9

This example envisages molecular machined formed by the fusion of ZOOANOTIC MEROZOITE derived peptide fragments whose function in nature is to bind with non human red blood cells, fused to CD4 segments in the manner already suggested.

Useful sources of peptides are

*Plasmodium Chabaudi*

*Plasmodium Yeolii*

*Plasmodium Berghei*

*Plasmodium Gallinacium*

*Plasmodium Cyanomogli*

The molecular machine so produced would be

| (ZOONOSIS) Animal parasite merozite derived RBC binding peptide | CD4 |
|---|---|

The amino acid sequences of such peptides are to be found in the Protein Data Bases together with restriction maps, in the public domain, available on payment; of a fee and incorporated fully herein by reference. Such novel molecular machines find a use in HIV testing Method of Use of Exemplary Embodiment 9

A sample of human blood to be tested is mixed with a known quantity of animal blood treated with the molecular machines of example 9.

The sample is agitated and thereafter the animal RBC removed selectively by anti-animal RBC antibodies bound to argarose or polyacrylamide gels or the like. Fluorescent labelled anti HIV antibody is then employed demonstrate virus particles adherent to the animal red cell. Quantification may then take place by automated systems in the usual way.

Experimental Verification

Experiment 1A

Immunological Characterisation Using Antibodies Directed Against CD4

Purified samples of the molecular machines in amounts ranging from 0.1 ug to 1 ug are used to coat the walls of ELISA plates and are thereafter incubated with preparations of OKT4A mAb (Ortho Diagnostics): the activity of the OKT4A are first altered by incubation with varying amounts of soluble CD4 preparations. A labelled anti-mouse serum is then used to assess the amount of bound mouse antibody.

Experiment 1B

Immunological Characterisation Using Antibodies Directed Against the Malaria Derived Component Purified samples of the molecular machines in amounts ranging from 0.1 ug to 1 ug are used to coat the walls of ELISA plates and are thereafter incubated with monoclonal antibodies directed against the erythrocyte binding peptide component. Binding is revealed by goat anti mouse antibodies the said goat antibodies to be labelled by conventional means.

Experiment 2

The Binding of the Disclosed Molecular Machines to Red Cell Surfaces

A buffered solution containing 100,000 human red cells is incubated with 20 ug of fusion peptides. The washed red cells are thereafter incubated with $1\times10^{11}$ M of OKT4A (Ortho Diagnostics). The RBC's are washed again with appropriate isotonic buffer and incubated with peroxidase labelled goat anti mouse IGG serum (BIOYSIS). Further washing and the addition of 3,3',5,5'-tetramethylbenzidine permits assessment of binding by the measurement of absorbance at 600 nm.

Experiment 3

The Binding Kinetics of RBC: and the Disclosed Molecular Machines

A known quantity of a purified sample of fusion peptide 0.1 ug to 1 ug in increments of ×2 are incubated with 100,000 RBC's in isotonic buffer solution. 125-I labelled OKT4A or otherwise labelled OKT4A are added at set times 1 min, 2 min, 4.8, 16, 30 min and 1 hour; the red cells are centrifuged through Percoll 2 minutes after the addition of 125-I labelled OKT4A. Accordingly both the optimum ratio of RBC to molecular machines can be calculated together with the binding time to saturation of each incremental dose of fusion peptides.

Experiment 4

The Binding of Live Virus to Red Cells Treated with the Disclosed Fusion Peptides 10 ml of whole blood drawn from HIV Elisa and WB negative blood donors is centrifuged after mixing with Alser-er's solution and rediluted to haematocrits of 25%, 35%, 45%, 55% and 65%, 75% this corresponding to the range of haematocrits seen in gross anaemia with dilution, to packed cells. The whole blood samples are incubated with amounts of fusion peptides ranging from 0.1 ug in increasing increments of ×2 to 10 ug. Thereafter the samples are incubated after mixing with 1 ml of suspension of cultured HIV-1 Bru particles having viral dose levels ranging from 50 to 50,000 viral particles per ml. Centrifugation is carried out after 60 minutes. The supernatant and red cell are separately assayed for bound virus using techniques already described, or by conventional means.

Experiment 5

In Vitro Demonstration of Clinical Utility 50 ml samples of blood are obtained from HIV positive and AIDS patients and divided into of 10 ml after appropriate buffering and anticoagulation. One 10 ml sample from each patient is assayed for viral titre levels by conventional means. The remaining 4 samples of 10 ml of blood from each patient are treated by molecular machines of exemplary embodiments 1, 2, 3, 4, 5, 6 and 8 in amounts ranging from 0.1 ug to 1 mg and thereafter assayed for viral titre levels by conventional means. Additional samples are centrifuged and the packed cells rediluted and assayed for viral titre levels separate from the plasma also assayed.

The invention claimed is:

1. A fusion protein comprising two or more components wherein the first component comprises the CD4 protein, or a substitution, deletion, or insertion analog or fragment of the CD4 protein, and the second component comprises the malaria parasite merozoite glycophorin binding protein 130 (GBP-130), or a substitution, deletion, or insertion analog or fragment of the GBP-130 protein thereof, wherein the CD4 component retains the ability to bind to the human immunodeficiency virus (HIV) envelope glycoprotein and the GBP-130 component retains the ability to bind to erythrocytes.

2. The fusion protein of claim 1, wherein the GBP-130 component is fused to the CD4 component either N- or C-terminally.

3. The fusion protein of claim 1, wherein the CD4 component is fused to the GBP component either N- or C-terminally.

4. The fusion protein of claim 1 wherein said protein comprises a linker between the first and second component.

5. The fusion protein of claim 1 wherein the fusion protein comprises amino acids 1-177 or 1-371 of CD4 fused to amino acids 201-774, 207-774, 227-774, or 370-425 of GBP-130.

6. The fusion protein according to claim 5 comprising the following formula: NH2-CD4(1-371)-GBP-130(201-774)-COOH.

7. The fusion protein according to claim 5 comprising the following formula: NH2-CD4(1-177)-GBP-130(201-774)-COOH.

8. The fusion protein according to claim 5 comprising the following formula: NH2-CD4(1-177)-GBP-130(1-74)-COOH.

9. The fusion protein according to claim 1 wherein a protein fragment comprising all or part of the amino acid sequence set forth in SEQ ID NO.: 6 is inserted between the CD4 and GBP-130 components.

* * * * *

```
                    SEQUENCE LISTING (1) GENERAL INFORMATION:

(iii) NUMBER OF SEQUENCES: 7

(2) INFORMATION FOR SEQ ID NO: 1:

(i) SEQUENCE CHARACTERISTICS:
          (A) LENGTH: 942 amino acids
          (B) TYPE: amino acid
          (D) TOPOLOGY: linear (ii) MOLECULE TYPE: protein
```

(iii) HYPOTHETICAL: YES (xi) SEQUENCE DESCRIPTION: SEQ ID NO: 1:

```
Gln Gly Asn Lys Val Val Leu Gly Lys Gly Asp Thr Val Glu Leu
1               5                   10                  15

Thr Cys Thr Ala Ser Gln Lys Ser Ile Gln Phe His Trp Lys Asn
                20                  25                  30

Ser Asn Gln Ile Lys Ile Leu Gly Asn Gln Gly Ser Phe Leu Thr Lys
            35                  40                  45

Gly Pro Ser Lys Leu Asn Asp Arg Ala Asp Ser Arg Arg Ser Leu Trp
50                  55                  60

Asp Gln Gly Asn Phe Pro Leu Ile Ile Lys Asn Leu Lys Ile Glu Asp
65                  70                  75                  80

Ser Asp Thr Tyr Ile Cys Glu Val Glu Asp Gln Lys Glu Glu Val Gln
                85                  90                  95

Leu Leu Val Phe Gly Leu Thr Ala Asn Ser Asp Thr His Leu Leu Gln
            100                 105                 110

Gly Gln Ser Leu Thr Leu Thr Leu Glu Ser Pro Pro Gly Ser Ser Pro
        115                 120                 125

Ser Val Gln Cys Arg Ser Pro Arg Gly Lys Asn Ile Gln Gly Gly Lys
        130                 135                 140

Thr Leu Ser Val Ser Gln Leu Glu Leu Gln Asp Ser Gly Thr Trp Thr
145                 150                 155                 160

Cys Thr Val Leu Gln Asn Gln Lys Lys Val Glu Phe Lys Ile Asp Ile
                165                 170                 175

Val Val Leu Ala Phe Gln Lys Ala Ser Ser Ile Val Tyr Lys Lys Glu
            180                 185                 190

Gly Glu Gln Val Glu Phe Ser Phe Pro Leu Ala Phe Thr Val Glu Lys
        195                 200                 205

Leu Thr Gly Ser Gly Glu Leu Trp Trp Gln Ala Glu Arg Ala Ser Ser
        210                 215                 220

Ser Lys Ser Trp Ile Thr Phe Asp Leu Lys Asn Lys Glu Val Ser Val
225                 230                 235                 240

Lys Arg Val Thr Gln Asp Pro Lys Leu Gln Met Gly Lys Lys Leu Pro
                245                 250                 255

Leu His Leu Thr Leu Pro Gln Ala Leu Pro Gln Tyr Ala Gly Ser Gly
            260                 265                 270

Asn Leu Thr Leu Ala Leu Glu Ala Lys Thr Gly Lys Leu His Gln Glu
        275                 280                 285

Val Asn Leu Val Val Met Arg Ala Thr Gln Leu Gln Lys Asn Leu Thr
        290                 295                 300

Cys Glu Val Trp Gly Pro Thr Ser Pro Lys Leu Met Leu Ser Leu Lys
305                 310                 315                 320

Leu Glu Asn Lys Glu Ala Lys Val Ser Lys Arg Glu Lys Ala Val Trp
                325                 330                 335

Val Leu Asn Pro Glu Ala Gly Met Trp Gln Cys Leu Leu Ser Asp Ser
            340                 345                 350

Gly Gln Val Leu Leu Glu Ser Asn Ile Lys Val Leu Pro Thr Trp Ser
        355                 360                 365

Thr Pro Val Ser Gln Lys Pro Ser Thr Thr Arg Ser Asn Asn Glu
        370                 375                 380

Val Lys Ile Arg Ala Ala Ser Asn Gln Glu Thr Leu Thr Ser Ala Asp
385                 390                 395                 400
```

-continued

```
Pro Glu Gly Gln Ile Met Arg Glu Tyr Ala Ala Asp Pro Glu Tyr Arg
                    405                 410                 415

Lys His Leu Glu Ile Phe Tyr Lys Ile Leu Thr Asn Thr Asp Pro Asn
                420                 425                 430

Asp Glu Val Glu Arg Arg Asn Ala Asp Asn Lys Glu Asp Leu Thr Ser
            435                 440                 445

Ala Asp Pro Glu Gly Gln Ile Met Arg Glu Tyr Ala Ser Asp Pro Glu
        450                 455                 460

Tyr Arg Lys His Leu Glu Ile Phe Tyr Lys Ile Leu Thr Asn Thr Asp
465                 470                 475                 480

Pro Asn Asp Asp Val Glu Arg Arg Asn Ala Asp Asn Lys Glu Asp Leu
                485                 490                 495

Thr Ser Ala Asp Pro Glu Gly Gln Ile Met Arg Glu Tyr Ala Ala Asp
                500                 505                 510

Pro Glu Tyr Arg Lys His Leu Glu Val Phe His Lys Ile Leu Thr Asn
                515                 520                 525

Thr Asp Pro Asn Asp Glu Val Glu Arg Arg Asn Ala Asp Asn Lys Glu
            530                 535                 540

Asp Leu Thr Ser Ala Asp Pro Glu Gly Gln Ile Met Arg Glu Tyr Ala
545                 550                 555                 560

Ala Asp Pro Glu Tyr Arg Lys His Leu Glu Ile Phe His Lys Ile Leu
                565                 570                 575

Thr Asn Thr Asp Pro Asn Asp Glu Val Glu Arg Arg Asn Ala Asp Asn
            580                 585                 590

Lys Glu Asp Leu Thr Ser Ala Asp Pro Glu Gly Gln Ile Met Arg Glu
            595                 600                 605

Tyr Ala Ala Asp Pro Glu Tyr Arg Lys His Leu Glu Val Phe His Lys
        610                 615                 620

Ile Leu Thr Asn Thr Asp Pro Asn Asp Glu Val Glu Arg Arg Asn Ala
625                 630                 635                 640

Asp Asn Lys Glu Leu Thr Ser Ser Asp Pro Glu Gly Gln Ile Met Arg
                645                 650                 655

Glu Tyr Ala Ala Asp Pro Glu Tyr Arg Lys His Leu Glu Ile Phe His
                660                 665                 670

Lys Ile Leu Thr Asn Thr Asp Pro Asn Asp Glu Val Glu Arg Arg Asn
            675                 680                 685

Ala Asp Asn Lys Glu Asp Leu Thr Ser Ala Asp Pro Glu Gly Gln Ile
        690                 695                 700

Met Arg Glu Tyr Ala Ala Asp Pro Glu Tyr Arg Lys His Leu Glu Ile
705                 710                 715                 720

Phe Tyr Lys Ile Leu Thr Asn Thr Asp Pro Asn Asp Glu Val Glu Arg
                725                 730                 735

Arg Asn Ala Asp Asn Lys Glu Asp Leu Thr Ser Ala Asp Pro Glu Gly
            740                 745                 750

Gln Ile Met Arg Glu Tyr Ala Ala Asp Pro Glu His Leu Glu Ile Phe
        755                 760                 765

His Lys Ile Leu Thr Asn Thr Asp Pro Asn Asp Glu Val Glu Arg Arg
    770                 775                 780

Asn Ala Asp Asn Lys Glu Glu Leu Thr Ser Ser Asp Pro Glu Gly Gln
785                 790                 795                 800

Ile Met Arg Glu Tyr Ala Ala Asp Pro Glu Tyr Arg Lys His Leu Glu
                805                 810                 815

Ile Phe Tyr Lys Ile Leu Thr Asn Thr Asp Pro Asn Asp Glu Val Glu
```

```
                  820                 825                 830
Arg Arg Asn Ala Asp Asn Lys Glu Asp Leu Thr Ser Ala Asp Pro Glu
            835                 840                 845

Gly Gln Ile Met Arg Glu Tyr Ala Ser Asp Pro Glu Tyr Arg Lys His
            850                 855                 860

Leu Glu Ile Phe Tyr Lys Ile Leu Thr Asn Thr Asp Pro Asn Asp Asp
865                 870                 875                 880

Val Glu Arg Arg Asn Ala Asp Asn Lys Glu Asp Leu Thr Ser Ala Asp
                885                 890                 895

Pro Gly Glu Gln Ile Met Arg Glu Tyr Ala Ala Asp Pro Glu Tyr Arg
            900                 905                 910

Lys His Leu Glu Ile Phe His Lys Ile Leu Thr Asn Thr Asp Pro Pro
            915                 920                 925

Asn Asp Glu Val Glu Arg Gln Asn Ala Asp Asn Glu Ala
            930                 935                 940

(2) INFORMATION FOR SEQ ID NO: 2:

(i) SEQUENCE CHARACTERISTICS:
        (A) LENGTH: 729 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO: 2:

Gln Gly Asn Lys Val Val Leu Gly Lys Lys Gly Asp Thr Val Glu Leu
1               5                   10                  15

Thr Cys Thr Ala Ser Gln Lys Lys Ser Ile Gln Phe His Trp Lys Asn
            20                  25                  30

Ser Asn Gln Ile Lys Ile Leu Gly Asn Gln Gly Ser Phe Leu Thr Lys
            35                  40                  45

Gly Pro Ser Lys Leu Asn Asp Arg Ala Asp Ser Arg Arg Ser Leu Trp
        50                  55                  60

Asp Gln Gly Asn Phe Pro Leu Ile Ile Lys Asn Leu Lys Ile Glu Asp
65              70                  75                  80

Ser Asp Thr Tyr Ile Cys Glu Val Glu Asp Gln Lys Glu Glu Val Gln
                85                  90                  95

Leu Leu Val Phe Gly Leu Thr Ala Asn Ser Asp Thr His Leu Leu Gln
            100                 105                 110

Gly Gln Ser Leu Thr Leu Thr Leu Glu Ser Pro Pro Gly Ser Ser Pro
            115                 120                 125

Ser Val Gln Cys Arg Ser Pro Arg Gly Lys Asn Ile Gln Gly Gly Lys
        130                 135                 140

Thr Leu Ser Val Ser Gln Leu Glu Leu Gln Asp Ser Gly Thr Trp Thr
145                 150                 155                 160

Cys Thr Val Leu Gln Asn Gln Lys Lys Val Glu Phe Lys Ile Asp Ile
                165                 170                 175

Val Val Leu Ala Phe Gln Lys Ala Ser Ser Ile Val Tyr Lys Lys Glu
            180                 185                 190

Gly Glu Gln Val Glu Phe Ser Phe Pro Leu Ala Phe Thr Val Glu Lys
            195                 200                 205

Leu Thr Gly Ser Gly Glu Leu Trp Trp Gln Ala Glu Arg Ala Ser Ser
        210                 215                 220
```

-continued

```
Ser Lys Ser Trp Ile Thr Phe Asp Leu Lys Asn Lys Glu Val Ser Val
225                 230                 235                 240

Lys Arg Val Thr Gln Asp Pro Lys Leu Gln Met Gly Lys Lys Leu Pro
            245                 250                 255

Leu His Leu Thr Leu Pro Gln Ala Leu Pro Gln Tyr Ala Gly Ser Gly
        260                 265                 270

Asn Leu Thr Leu Ala Leu Glu Ala Lys Thr Gly Lys Leu His Gln Glu
    275                 280                 285

Val Asn Leu Val Val Met Arg Ala Thr Gln Leu Gln Lys Asn Leu Thr
290                 295                 300

Cys Glu Val Trp Gly Pro Thr Ser Pro Lys Leu Met Leu Ser Leu Lys
305                 310                 315                 320

Leu Glu Asn Lys Glu Ala Lys Val Ser Lys Arg Glu Lys Ala Val Trp
            325                 330                 335

Val Leu Asn Pro Glu Ala Gly Met Trp Gln Cys Leu Leu Ser Asp Ser
        340                 345                 350

Gly Gln Val Leu Leu Glu Ser Asn Ile Lys Val Leu Pro Thr Trp Ser
    355                 360                 365

Thr Pro Val Ser Gln Tyr Lys Gln Ala Ala Asp Tyr Ser Phe Arg Glu
370                 375                 380

Ser Arg Val Leu Ala Glu Gly Lys Ser Thr Ser Lys Lys Asn Ala Lys
385                 390                 395                 400

Thr Ala Leu Arg Lys Thr Lys Gln Thr Thr Leu Thr Ser Ala Asp Pro
            405                 410                 415

Glu Gly Gln Ile Met Lys Ala Trp Ala Ala Asp Pro Glu Tyr Arg Lys
        420                 425                 430

His Leu Asn Val Leu Tyr Gln Ile Leu Asn Asn Thr Asp Pro Asn Asp
    435                 440                 445

Glu Leu Glu Thr Ser Ala Asp Pro Glu Gly Gln Ile Met Lys Ala Tyr
450                 455                 460

Ala Ala Asp Pro Glu Tyr Arg Lys His Leu Asn Val Leu Tyr Gln Ile
465                 470                 475                 480

Leu Asn Asn Thr Asp Pro Asn Asp Glu Val Glu Ser Ser Ala Asp Pro
            485                 490                 495

Glu Gly Gln Ile Met Lys Ala Tyr Ala Ala Asp Pro Glu Tyr Arg Lys
        500                 505                 510

His Val Asn Val Leu Tyr Gln Ile Leu Asn Asn Thr Asp Pro Asn Asp
    515                 520                 525

Glu Leu Glu Thr Ser Ala Asp Pro Glu Gly Gln Ile Met Lys Ala Tyr
530                 535                 540

Ala Ala Asp Pro Glu Tyr Arg Lys His Val Asn Val Leu Tyr Gln Ile
545                 550                 555                 560

Leu Asn His Thr Asp Ser Ser Glu Val Glu Thr Ser Ala Asp Pro Glu
            565                 570                 575

Gly Gln Ile Met Lys Ala Tyr Ala Ala Asp Pro Glu Tyr Arg Lys His
        580                 585                 590

Val Asn Val Leu Tyr Gln Ile Leu Asn His Thr Asp Ser Ser Glu Val
    595                 600                 605

Glu Thr Ser Ala Asp Pro Glu Gly Gln Ile Met Lys Ala Tyr Ala Ala
610                 615                 620

Asp Pro Glu Tyr Arg Lys His Val Asn Val Leu Tyr Gln Ile Leu Asn
625                 630                 635                 640

Asn Thr Asp Pro Asn Asp Glu Leu Glu Thr Ser Ala Asp Pro Glu Gly
```

```
                    645                 650                 655
Gln Ile Met Lys Ala Tyr Ala Ala Asp Pro Glu Tyr Arg Lys His Val
                660                 665                 670

Asn Val Leu Tyr Gln Ile Leu Asn Asn Thr Asp Pro Asn Asp Glu Leu
                675                 680                 685

Glu Thr Ser Ala Asp Pro Glu Gly Gln Ile Met Lys Ala Tyr Ala Ala
            690                 695                 700

Asp Pro Glu Tyr Arg Lys His Val Asn Val Leu Tyr Gln Ile Leu Asn
705                 710                 715                 720

Asn Thr Asp Pro Asn Asp Glu Ser Ser
                725

(2) INFORMATION FOR SEQ ID NO: 3:

(i) SEQUENCE CHARACTERISTICS:
        (A) LENGTH: 1786 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO: 3:

Gln Gly Asn Lys Val Val Leu Gly Lys Lys Gly Asp Thr Val Glu Leu
1               5                   10                  15

Thr Cys Thr Ala Ser Gln Lys Lys Ser Ile Gln Phe His Trp Lys Asn
                20                  25                  30

Ser Asn Gln Ile Lys Ile Leu Gly Asn Gln Gly Ser Phe Leu Thr Lys
            35                  40                  45

Gly Pro Ser Lys Leu Asn Asp Arg Ala Asp Ser Arg Arg Ser Leu Trp
        50                  55                  60

Asp Gln Gly Asn Phe Pro Leu Ile Ile Lys Asn Leu Lys Ile Glu Asp
65                  70                  75                  80

Ser Asp Thr Tyr Ile Cys Glu Val Glu Asp Gln Lys Glu Glu Val Gln
                85                  90                  95

Leu Leu Val Phe Gly Leu Thr Ala Asn Ser Asp Thr His Leu Leu Gln
                100                 105                 110

Gly Gln Ser Leu Thr Leu Thr Leu Glu Ser Pro Pro Gly Ser Ser Pro
            115                 120                 125

Ser Val Gln Cys Arg Ser Pro Arg Gly Lys Asn Ile Gln Gly Gly Lys
        130                 135                 140

Thr Leu Ser Val Ser Gln Leu Glu Leu Gln Asp Ser Gly Thr Trp Thr
145                 150                 155                 160

Cys Thr Val Leu Gln Asn Gln Lys Lys Val Glu Phe Lys Ile Asp Ile
                165                 170                 175

Val Val Leu Ala Phe Gln Lys Ala Ser Ser Ile Val Tyr Lys Lys Glu
            180                 185                 190

Gly Glu Gln Val Glu Phe Ser Phe Pro Leu Ala Phe Thr Val Glu Lys
        195                 200                 205

Leu Thr Gly Ser Gly Glu Leu Trp Trp Gln Ala Glu Arg Ala Ser Ser
    210                 215                 220

Ser Lys Ser Trp Ile Thr Phe Asp Leu Lys Asn Lys Glu Val Ser Val
225                 230                 235                 240

Lys Arg Val Thr Gln Asp Pro Lys Leu Gln Met Gly Lys Lys Leu Pro
                245                 250                 255
```

```
Leu His Leu Thr Leu Pro Gln Ala Leu Pro Gln Tyr Ala Gly Ser Gly
            260                 265                 270

Asn Leu Thr Leu Ala Leu Glu Ala Lys Thr Gly Lys Leu His Gln Glu
        275                 280                 285

Val Asn Leu Val Val Met Arg Ala Thr Gln Leu Gln Lys Asn Leu Thr
    290                 295                 300

Cys Glu Val Trp Gly Pro Thr Ser Pro Lys Leu Met Leu Ser Leu Lys
305                 310                 315                 320

Leu Glu Asn Lys Glu Ala Lys Val Ser Lys Arg Glu Lys Ala Val Trp
                325                 330                 335

Val Leu Asn Pro Glu Ala Gly Met Trp Gln Cys Leu Leu Ser Asp Ser
            340                 345                 350

Gly Gln Val Leu Leu Glu Ser Asn Ile Lys Val Leu Pro Thr Trp Ser
        355                 360                 365

Thr Pro Val Lys Ala Arg Asn Glu Tyr Asp Ile Lys Glu Asn Glu Lys
    370                 375                 380

Phe Leu Asp Val Tyr Lys Glu Lys Phe Asn Glu Leu Asp Lys Lys Lys
385                 390                 395                 400

Tyr Gly Asn Val Gln Lys Thr Asp Lys Lys Ile Phe Thr Phe Ile Glu
                405                 410                 415

Asn Lys Leu Asp Ile Leu Asn Asn Ser Lys Phe Asn Lys Arg Trp Lys
            420                 425                 430

Ser Tyr Gly Thr Pro Asp Asn Ile Asp Lys Asn Met Ser Leu Ile Asn
        435                 440                 445

Lys His Asn Asn Glu Glu Met Phe Asn Asn Asn Tyr Gln Ser Phe Leu
    450                 455                 460

Ser Thr Ser Ser Leu Ile Lys Gln Asn Lys Tyr Val Pro Ile Asn Ala
465                 470                 475                 480

Val Arg Val Ser Arg Ile Leu Ser Phe Leu Asp Ser Arg Ile Asn Asn
                485                 490                 495

Gly Arg Asn Thr Ser Ser Asn Asn Glu Val Leu Ser Asn Cys Arg Glu
            500                 505                 510

Lys Arg Lys Gly Met Lys Trp Asp Cys Lys Lys Asn Asp Arg Ser
    515                 520                 525

Asn Tyr Val Cys Ile Pro Asp Arg Arg Ile Gln Leu Cys Ile Val Asn
530                 535                 540

Leu Ser Ile Ile Lys Thr Tyr Thr Lys Glu Thr Met Lys Asp His Phe
545                 550                 555                 560

Ile Glu Ala Ser Lys Lys Glu Ser Gln Leu Leu Leu Lys Lys Asn Asp
                565                 570                 575

Asn Lys Tyr Asn Ser Lys Phe Cys Asn Asp Leu Lys Asn Ser Phe Leu
            580                 585                 590

Asp Tyr Gly His Leu Ala Met Gly Asn Asp Met Asp Phe Gly Gly Tyr
        595                 600                 605

Ser Thr Lys Ala Glu Asn Lys Ile Gln Glu Val Phe Lys Gly Ala His
    610                 615                 620

Gly Glu Ile Ser Glu His Lys Ile Lys Asn Phe Arg Lys Glu Trp Trp
625                 630                 635                 640

Asn Glu Phe Arg Glu Lys Leu Trp Glu Ala Met Leu Ser Glu His Lys
                645                 650                 655

Asn Asn Ile Asn Asn Cys Lys Asn Ile Pro Gln Glu Glu Leu Gln Ile
            660                 665                 670

Thr Gln Trp Ile Lys Glu Trp His Gly Glu Phe Leu Leu Glu Arg Asp
```

-continued

```
                675                 680                 685
Asn Arg Ser Lys Leu Pro Lys Ser Lys Cys Lys Asn Asn Thr Leu Tyr
690                 695                 700
Glu Ala Cys Glu Lys Glu Cys Ile Asp Pro Cys Met Lys Tyr Arg Asp
705                 710                 715                 720
Trp Ile Ile Arg Ser Lys Phe Glu Trp His Thr Leu Ser Lys Glu Tyr
                725                 730                 735
Glu Thr Gln Lys Val Pro Lys Glu Asn Ala Glu Asn Tyr Leu Ile Lys
                740                 745                 750
Ile Ser Glu Asn Lys Asn Asp Ala Lys Val Ser Leu Leu Asn Asn
            755                 760                 765
Cys Asp Ala Glu Tyr Ser Lys Tyr Cys Asp Cys Lys His Thr Thr Thr
770                 775                 780
Leu Val Lys Ser Val Leu Asn Gly Asn Asp Asn Thr Ile Lys Glu Lys
785                 790                 795                 800
Arg Glu His Ile Asp Leu Asp Asp Phe Ser Lys Phe Gly Cys Asp Lys
                805                 810                 815
Asn Ser Val Asp Thr Asn Thr Lys Val Trp Glu Cys Lys Asn Pro Tyr
            820                 825                 830
Ile Leu Ser Thr Lys Asp Val Cys Val Pro Pro Arg Arg Gln Glu Leu
            835                 840                 845
Cys Leu Gly Asn Ile Asp Arg Ile Tyr Asp Lys Asn Leu Leu Met Ile
850                 855                 860
Lys Glu His Ile Leu Ala Ile Ala Ile Tyr Glu Ser Arg Ile Leu Lys
865                 870                 875                 880
Arg Lys Tyr Lys Asn Lys Asp Asp Lys Glu Val Cys Lys Ile Ile Asn
                885                 890                 895
Lys Thr Phe Ala Asp Ile Arg Asp Ile Ile Gly Gly Thr Asp Tyr Trp
                900                 905                 910
Asn Asp Leu Ser Asn Arg Lys Leu Val Gly Lys Ile Asn Thr Asn Ser
            915                 920                 925
Lys Tyr Val His Arg Asn Lys Lys Asn Asp Lys Leu Phe Arg Asp Glu
930                 935                 940
Trp Trp Lys Val Ile Lys Lys Asp Val Trp Asn Val Ile Ser Trp Val
945                 950                 955                 960
Phe Lys Asp Lys Thr Val Cys Lys Glu Asp Ile Glu Asn Ile Pro
                965                 970                 975
Gln Phe Phe Arg Trp Phe Ser Glu Trp Gly Asp Tyr Cys Gln Asp
                980                 985                 990
Lys Thr Lys Met Ile Glu Thr Leu Lys Val Glu Cys Lys Glu Lys Pro
            995                 1000                1005
Cys Glu Asp Asp Asn Cys Lys Ser Lys Cys Asn Ser Tyr Lys Glu Trp
        1010                1015                1020
Ile Ser Lys Lys Lys Glu Glu Tyr Asn Lys Gln Ala Lys Gln Tyr Gln
1025                1030                1035                1040
Glu Tyr Gln Lys Gly Asn Asn Tyr Lys Met Tyr Ser Glu Phe Lys Ser
                1045                1050                1055
Ile Lys Pro Glu Val Tyr Leu Lys Lys Tyr Ser Glu Lys Cys Ser Asn
                1060                1065                1070
Leu Asn Phe Glu Asp Glu Phe Lys Glu Glu Leu His Ser Asp Tyr Lys
            1075                1080                1085
Asn Lys Cys Thr Met Cys Pro Glu Val Lys Asp Val Pro Ile Ser Ile
            1090                1095                1100
```

-continued

```
Ile Arg Asn Asn Glu Gln Thr Ser Gln Glu Ala Val Pro Glu Glu Asn
1105                1110                1115                1120

Thr Glu Ile Ala His Arg Thr Glu Thr Pro Ser Ile Ser Glu Gly Pro
            1125                1130                1135

Lys Gly Asn Glu Gln Lys Glu Arg Asp Asp Asp Ser Leu Ser Lys Ile
        1140                1145                1150

Ser Val Ser Pro Glu Asn Ser Arg Pro Glu Thr Asp Ala Lys Asp Thr
    1155                1160                1165

Ser Asn Leu Leu Lys Leu Lys Gly Asp Val Asp Ile Ser Met Pro Lys
1170                1175                1180

Ala Val Ile Gly Ser Ser Pro Asn Asp Asn Ile Asn Val Thr Glu Gln
1185                1190                1195                1200

Gly Asp Asn Ile Ser Gly Val Asn Ser Lys Pro Leu Ser Asp Asp Val
            1205                1210                1215

Arg Pro Asp Lys Lys Glu Leu Glu Asp Gln Asn Ser Asp Glu Ser Glu
        1220                1225                1230

Glu Thr Val Val Asn His Ile Ser Lys Ser Pro Ser Ile Asn Asn Gly
    1235                1240                1245

Asp Asp Ser Gly Ser Gly Ser Ala Thr Val Ser Glu Ser Ser Ser Asn
1250                1255                1260

Thr Gly Leu Ser Ile Asp Asp Arg Asn Gly Asp Thr Phe Val Arg
1265                1270                1275                1280

Thr Gln Asp Thr Ala Asn Thr Glu Asp Val Ile Arg Lys Glu Asn Ala
            1285                1290                1295

Asp Lys Asp Glu Asp Glu Lys Gly Ala Asp Glu Glu Arg His Ser Thr
        1300                1305                1310

Ser Glu Ser Leu Ser Ser Pro Glu Glu Lys Met Leu Thr Asp Asn Glu
    1315                1320                1325

Gly Gly Asn Ser Leu Asn His Glu Glu Val Lys Glu His Thr Ser Asn
1330                1335                1340

Ser Asp Asn Val Gln Gln Ser Gly Gly Ile Val Asn Met Asn Val Glu
1345                1350                1355                1360

Lys Glu Leu Lys Asp Thr Leu Glu Asn Pro Ser Ser Ser Leu Asp Glu
            1365                1370                1375

Gly Lys Ala His Glu Glu Leu Ser Glu Pro Asn Leu Ser Ser Asp Gln
        1380                1385                1390

Asp Met Ser Asn Thr Pro Gly Pro Leu Asp Asn Thr Ser Glu Glu Thr
    1395                1400                1405

Thr Glu Arg Ile Ser Asn Asn Glu Tyr Lys Val Asn Glu Arg Glu Asp
1410                1415                1420

Glu Arg Thr Leu Thr Lys Glu Tyr Glu Asp Ile Val Leu Lys Ser His
1425                1430                1435                1440

Met Asn Arg Glu Ser Asp Asp Gly Glu Leu Tyr Asp Glu Asn Ser Asp
            1445                1450                1455

Leu Ser Thr Val Asn Asp Glu Ser Glu Asp Ala Glu Ala Lys Met Lys
        1460                1465                1470

Gly Asn Asp Thr Ser Glu Met Ser His Asn Ser Ser Gln His Ile Glu
    1475                1480                1485

Ser Asp Gln Gln Lys Asn Asp Met Lys Thr Val Gly Asp Leu Gly Thr
1490                1495                1500

Thr His Val Gln Asn Glu Ile Ser Val Pro Val Thr Gly Glu Ile Asp
1505                1510                1515                1520
```

-continued

```
Glu Lys Leu Arg Glu Ser Lys Glu Ser Lys Ile His Lys Ala Glu Glu
            1525                1530                1535

Glu Arg Leu Ser His Thr Asp Ile His Lys Ile Asn Pro Glu Asp Arg
            1540                1545                1550

Asn Ser Asn Thr Leu His Leu Lys Asp Ile Arg Asn Glu Glu Asn Glu
            1555                1560                1565

Arg His Leu Thr Asn Gln Asn Ile Asn Ile Ser Gln Glu Arg Asp Leu
            1570                1575                1580

Gln Lys His Gly Phe His Thr Met Asn Asn Leu His Gly Asp Gly Val
1585                1590                1595                1600

Ser Glu Arg Ser Gln Ile Asn His Ser His Gly Asn Arg Gln Asp
            1605                1610                1615

Arg Gly Gly Asn Ser Gly Asn Val Leu Asn Met Arg Ser Asn Asn Asn
            1620                1625                1630

Asn Phe Asn Asn Ile Pro Ser Arg Tyr Asn Leu Tyr Asp Lys Lys Leu
            1635                1640                1645

Asp Leu Asp Leu Tyr Glu Asn Arg Asn Asp Ser Thr Thr Lys Glu Leu
            1650                1655                1660

Ile Lys Lys Leu Ala Glu Ile Asn Lys Cys Glu Asn Glu Ile Ser Val
1665                1670                1675                1680

Lys Tyr Cys Asp His Met Ile His Glu Glu Ile Pro Leu Lys Thr Cys
            1685                1690                1695

Thr Lys Glu Lys Thr Arg Asn Leu Cys Cys Ala Val Ser Asp Tyr Cys
            1700                1705                1710

Met Ser Tyr Phe Thr Tyr Asp Ser Glu Glu Tyr Tyr Asn Cys Thr Lys
            1715                1720                1725

Arg Glu Phe Asp Asp Pro Ser Tyr Thr Cys Phe Arg Lys Glu Ala Phe
            1730                1735                1740

Ser Ser Met Ile Phe Lys Phe Leu Ile Thr Asn Lys Ile Tyr Tyr Tyr
1745                1750                1755                1760

Phe Tyr Thr Tyr Lys Thr Ala Lys Val Thr Ile Lys Lys Ile Asn Phe
            1765                1770                1775

Ser Leu Ile Phe Phe Phe Phe Ser Phe
            1780                1785

(2) INFORMATION FOR SEQ ID NO: 4:

(i) SEQUENCE CHARACTERISTICS:
        (A) LENGTH: 1028 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO: 4:

Lys Asp Asp Phe Ser Ile Thr Leu Ile Asn Tyr His Glu Gly Lys Lys
1               5                   10                  15

Tyr Leu Ile Ile Leu Lys Arg Lys Leu Glu Lys Ala Asn Asn Arg Asp
            20                  25                  30

Val Cys Asn Phe Phe Leu His Phe Ser Gln Val Asn Asn Val Leu Leu
            35                  40                  45

Glu Arg Thr Ile Glu Thr Leu Leu Glu Cys Lys Asn Glu Tyr Val Lys
        50                  55                  60

Gly Glu Asn Gly Tyr Lys Leu Ala Lys Gly His His Cys Val Glu Glu
65              70                  75                  80
```

-continued

```
Asp Asn Leu Glu Arg Trp Leu Gln Gly Thr Asn Glu Arg Arg Ser Glu
                85                  90                  95
Glu Asn Ile Lys Tyr Lys Tyr Gly Val Thr Glu Leu Lys Ile Lys Tyr
            100                 105                 110
Ala Gln Met Asn Gly Lys Arg Ser Arg Ile Leu Lys Glu Ser Ile
        115                 120                 125
Tyr Gly Ala His Asn Phe Gly Gly Asn Ser Tyr Met Glu Gly Lys Asp
    130                 135                 140
Gly Gly Asp Lys Thr Gly Glu Glu Lys Asp Gly Glu His Lys Thr Asp
145                 150                 155                 160
Ser Lys Thr Asp Asn Gly Lys Gly Ala Asn Asn Leu Val Met Leu Asp
                165                 170                 175
Tyr Glu Thr Ser Ser Asn Gly Gln Pro Ala Gly Thr Leu Asp Asn Val
            180                 185                 190
Leu Glu Phe Val Thr Gly His Glu Gly Asn Ser Arg Lys Asn Ser Ser
        195                 200                 205
Asn Gly Gly Asn Pro Tyr Asp Ile Asp His Lys Lys Thr Ile Ser Ser
    210                 215                 220
Ala Ile Ile Asn His Ala Phe Leu Gln Asn Thr Val Met Lys Asn Cys
225                 230                 235                 240
Asn Tyr Lys Arg Lys Arg Arg Glu Arg Asp Trp Asp Cys Asn Thr Lys
                245                 250                 255
Lys Asp Val Cys Ile Pro Asp Arg Arg Tyr Gln Leu Cys Met Lys Glu
            260                 265                 270
Leu Thr Asn Leu Val Asn Asn Thr Asp Thr Asn Phe His Arg Asp Ile
        275                 280                 285
Thr Phe Arg Lys Leu Tyr Leu Lys Arg Lys Leu Ile Tyr Asp Ala Ala
    290                 295                 300
Val Glu Gly Asp Leu Leu Leu Lys Leu Asn Asn Tyr Arg Tyr Asn Lys
305                 310                 315                 320
Asp Phe Cys Lys Asp Ile Arg Trp Ser Leu Gly Asp Phe Gly Asp Ile
                325                 330                 335
Ile Met Gly Thr Asp Met Glu Gly Ile Gly Tyr Ser Lys Val Val Glu
            340                 345                 350
Asn Asn Leu Arg Ser Ile Phe Gly Thr Asp Glu Lys Ala Gln Gln Arg
        355                 360                 365
Arg Lys Gln Trp Trp Asn Glu Ser Lys Ala Gln Ile Trp Thr Ala Met
    370                 375                 380
Met Tyr Ser Val Lys Lys Arg Leu Lys Gly Asn Phe Ile Trp Ile Cys
385                 390                 395                 400
Lys Leu Asn Val Ala Val Asn Ile Glu Pro Gln Ile Tyr Arg Trp Ile
                405                 410                 415
Arg Glu Trp Gly Arg Asp Tyr Val Ser Glu Leu Pro Thr Glu Val Gln
            420                 425                 430
Lys Leu Lys Glu Lys Cys Asp Gly Lys Ile Asn Tyr Thr Asp Lys Lys
        435                 440                 445
Val Cys Lys Val Pro Pro Cys Gln Asn Ala Cys Lys Ser Tyr Asp Gln
    450                 455                 460
Trp Ile Thr Arg Lys Lys Asn Gln Trp Asp Val Leu Ser Asn Lys Phe
465                 470                 475                 480
Ile Ser Val Lys Asn Ala Glu Lys Val Gln Thr Ala Gly Ile Val Thr
                485                 490                 495
```

```
Pro Tyr Asp Ile Leu Lys Gln Glu Leu Asp Glu Phe Asn Glu Val Ala
        500                 505                 510
Phe Glu Asn Glu Ile Asn Lys Arg Asp Gly Ala Tyr Ile Glu Leu Cys
        515                 520                 525
Val Cys Ser Val Glu Glu Ala Lys Lys Asn Thr Gln Glu Val Val Thr
        530                 535                 540
Asn Val Asp Asn Ala Ala Lys Ser Gln Ala Thr Asn Ser Asn Pro Ile
545                 550                 555                 560
Ser Gln Pro Val Asp Ser Ser Lys Ala Glu Lys Val Pro Gly Asp Ser
                565                 570                 575
Thr His Gly Asn Val Asn Ser Gly Gln Asp Ser Ser Thr Thr Gly Lys
                580                 585                 590
Ala Val Thr Gly Asp Gly Gln Asn Gly Asn Gln Thr Pro Ala Glu Ser
            595                 600                 605
Asp Val Gln Arg Ser Asp Ile Ala Glu Ser Val Ser Ala Lys Asn Val
        610                 615                 620
Asp Pro Gln Lys Ser Val Ser Lys Arg Ser Asp Thr Ala Ser Val
625                 630                 635                 640
Thr Gly Ile Ala Glu Ala Gly Lys Glu Asn Leu Gly Ala Ser Asn Ser
                645                 650                 655
Arg Pro Ser Glu Ser Thr Val Glu Ala Asn Ser Pro Gly Asp Asp Thr
            660                 665                 670
Val Asn Ser Ala Ser Ile Pro Val Val Ser Gly Glu Asn Pro Leu Val
        675                 680                 685
Thr Pro Tyr Asn Gly Leu Arg His Ser Lys Asp Asn Ser Asp Ser Asp
        690                 695                 700
Gly Pro Ala Glu Ser Met Ala Asn Pro Asp Ser Asn Ser Lys Gly Glu
705                 710                 715                 720
Thr Gly Lys Gly Gln Asp Asn Asp Met Ala Lys Ala Thr Lys Asp Ser
                725                 730                 735
Ser Asn Ser Ser Asp Gly Thr Ser Ser Ala Thr Gly Asp Thr Thr Asp
                740                 745                 750
Ala Val Asp Arg Glu Ile Asn Lys Gly Val Pro Glu Asp Arg Asp Lys
            755                 760                 765
Thr Val Gly Ser Lys Asp Gly Gly Glu Asp Asn Ser Ala Asn Lys
        770                 775                 780
Asp Ala Ala Thr Val Val Gly Glu Asp Arg Ile Arg Glu Asn Ser Ala
785                 790                 795                 800
Gly Gly Ser Thr Asn Asp Arg Ser Lys Asn Asp Thr Glu Lys Asn Gly
                805                 810                 815
Ala Ser Thr Pro Asp Ser Lys Gln Ser Glu Asp Ala Thr Ala Leu Ser
            820                 825                 830
Lys Thr Glu Ser Leu Glu Ser Thr Glu Ser Gly Asp Arg Thr Thr Asn
        835                 840                 845
Asp Thr Thr Asn Ser Leu Glu Asn Lys Asn Gly Gly Lys Glu Lys Asp
        850                 855                 860
Leu Gln Lys His Asp Phe Lys Ser Asn Asp Thr Pro Asn Glu Pro
865                 870                 875                 880
Asn Ser Asp Gln Thr Thr Asp Ala Glu Gly His Asp Arg Asp Ser Ile
                885                 890                 895
Lys Asn Asp Lys Ala Glu Arg Arg Lys His Met Asn Lys Asp Thr Phe
            900                 905                 910
Thr Lys Asn Thr Asn Ser His His Leu Asn Ser Asn Asn Asn Leu Ser
```

-continued

```
                915                 920                 925
Asn Gly Lys Leu Asp Ile Lys Glu Tyr Lys Tyr Arg Asp Val Lys Ala
    930                 935                 940
Thr Arg Glu Asp Ile Ile Leu Met Ser Ser Val Arg Lys Cys Asn Asn
945                 950                 955                 960
Asn Ile Ser Leu Glu Tyr Cys Asn Ser Val Glu Asp Lys Ile Ser Ser
                965                 970                 975
Asn Thr Cys Ser Arg Glu Lys Ser Lys Asn Leu Cys Cys Ser Ile Ser
            980                 985                 990
Asp Phe Cys Leu Asn Tyr Phe Asp Val Tyr Ser Tyr Glu Tyr Leu Ser
        995                 1000                1005
Cys Met Lys Lys Glu Phe Glu Asp Pro Ser Tyr Lys Cys Phe Thr Lys
    1010                1015                1020
Gly Gly Phe Lys
1025

(2) INFORMATION FOR SEQ ID NO: 5:

(i) SEQUENCE CHARACTERISTICS:
        (A) LENGTH: 363 amino acids
        (B) TYPE: amino acid
        (D) TOPOLOGY: linear (ii) MOLECULE TYPE: protein (iii) HYPOTHETICAL: YES (xi) SEQUENCE DESCRIPTION: SEQ ID NO: 5:

Gln Gly Asn Lys Val Val Leu Gly Lys Lys Gly Asp Thr Val Glu Leu
1               5                   10                  15
Cys Thr Ala Ser Gln Lys Lys Ser Ile Gln Phe His Trp Lys Asn Ser
            20                  25                  30
Asn Gln Ile Lys Ile Leu Gly Asn Gln Gly Ser Phe Leu Thr Lys Gly
        35                  40                  45
Pro Ser Lys Leu Asn Asp Arg Ala Asp Ser Arg Arg Ser Leu Trp Asp
    50                  55                  60
Gln Gly Asn Phe Pro Leu Ile Ile Lys Asn Leu Lys Ile Glu Asp Ser
65                  70                  75                  80
Asp Thr Tyr Ile Cys Glu Val Glu Asp Gln Lys Glu Glu Val Gln Leu
                85                  90                  95
Leu Val Phe Gly Leu Thr Ala Asn Ser Asp Thr His Leu Leu Gln Gly
            100                 105                 110
Gln Ser Leu Thr Leu Thr Leu Glu Ser Pro Pro Gly Ser Ser Pro Ser
        115                 120                 125
Val Gln Cys Arg Ser Pro Arg Gly Lys Asn Ile Gln Gly Gly Lys Thr
    130                 135                 140
Leu Ser Val Ser Gln Leu Glu Leu Gln Asp Ser Gly Thr Trp Thr Cys
145                 150                 155                 160
Thr Val Leu Gln Asn Gln Lys Lys Val Glu Phe Lys Ile Asp Ile Val
                165                 170                 175
Val Leu Ala Phe Gln Lys Ala Ser Ser Ile Val Tyr Lys Lys Glu Gly
            180                 185                 190
Glu Gln Val Glu Phe Ser Phe Pro Leu Ala Phe Thr Val Glu Lys Leu
        195                 200                 205
Thr Gly Ser Gly Glu Leu Trp Trp Gln Ala Glu Arg Ala Ser Ser Ser
    210                 215                 220
```

-continued

```
Lys Ser Trp Ile Thr Phe Asp Leu Lys Asn Lys Glu Val Ser Val Lys
225                 230                 235                 240

Arg Val Thr Gln Asp Pro Lys Leu Gln Met Gly Lys Lys Leu Pro Leu
                245                 250                 255

His Leu Thr Leu Pro Gln Ala Leu Pro Gln Tyr Ala Gly Ser Gly Asn
                260                 265                 270

Asn Thr Leu Ala Leu Glu Ala Lys Thr Gly Lys Leu His Gln Glu Val
            275                 280                 285

Asn Leu Val Val Met Arg Ala Thr Gln Leu Gln Lys Asn Leu Thr Cys
        290                 295                 300

Glu Val Trp Gly Pro Thr Ser Pro Lys Leu Met Leu Ser Leu Lys Leu
305                 310                 315                 320

Glu Asn Lys Glu Ala Lys Val Ser Lys Arg Glu Lys Ala Val Trp Val
                325                 330                 335

Leu Asn Pro Glu Ala Gly Met Trp Gln Cys Leu Leu Ser Asp Ser Gly
                340                 345                 350

Gln Val Leu Leu Glu Ser Asn Ile Lys Val Leu
                355                 360
```

(2) INFORMATION FOR SEQ ID NO: 6:

(i) SEQUENCE CHARACTERISTICS:
        (A) LENGTH: 327 amino acids
        (B) TYPE: amino acid
        (D) TOPOLOGY: linear (ii) MOLECULE TYPE: protein (iii) HYPOTHETICAL: YES (v) FRAGMENT TYPE: internal (xi) SEQUENCE DESCRIPTION: SEQ ID NO: 6:

```
Ser Thr Lys Gly Pro Ser Val Phe Pro Leu Ala Pro Ser Ser Lys Ser
1               5                   10                  15

Thr Ser Gly Gly Thr Ala Ala Leu Gly Cys Leu Val Lys Asp Tyr Phe
                20                  25                  30

Pro Glu Pro Val Thr Val Ser Tyr Asn Ser Gly Ala Leu Thr Ser Gly
            35                  40                  45

Val His Thr Phe Pro Ala Val Leu Gln Ser Ser Gly Leu Tyr Ser Leu
        50                  55                  60

Ser Ser Val Val Thr Val Pro Ser Ser Ser Leu Gly Thr Gln Thr Tyr
65                  70                  75                  80

Ile Cys Asn Val Asn His Lys Pro Ser Asn Thr Leu Val Asp Lys Lys
                85                  90                  95

Val Glu Pro Lys Ser Cys Asp Lys Thr His Thr Cys Pro Pro Cys Pro
                100                 105                 110

Ala Pro Glu Leu Leu Gly Gly Pro Ser Val Phe Leu Phe Pro Pro Lys
            115                 120                 125

Pro Lys Asp Thr Leu Met Ile Ser Arg Thr Pro Glu Val Thr Cys Val
        130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Gln
                165                 170                 175

Tyr Asn Ser Thr Tyr Arg Val Val Ser Val Leu Thr Val Leu His Gln
            180                 185                 190
```

-continued

```
Asp Trp Leu Asn Gly Lys Glu Tyr Lys Cys Lys Val Ser Asn Lys Ala
        195                 200                 205

Leu Pro Ala Pro Ile Glu Lys Thr Ile Ser Lys Ala Lys Gly Gln Pro
    210                 215                 220

Arg Glu Pro Gln Val Tyr Thr Leu Pro Pro Ser Arg Asp Glu Leu Tyr
225                 230                 235                 240

Lys Asn Gln Val Ser Leu Thr Cys Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

(2) INFORMATION FOR SEQ ID NO: 7:

(i) SEQUENCE CHARACTERISTICS:
          (A) LENGTH: 19 amino acids
          (B) TYPE: amino acid
          (D) TOPOLOGY: linear (ii) MOLECULE TYPE: protein (iii) HYPOTHETICAL: YES (xi) SEQUENCE DESCRIPTION: SEQ ID NO: 7:

Val Gln Leu Leu Val Phe Gly Leu Thr Ala Asn Asn Ser Asp Thr His
1               5                   10                  15

Leu Leu Gln
```